US007309687B1

(12) United States Patent
Brines et al.

(10) Patent No.: US 7,309,687 B1
(45) Date of Patent: Dec. 18, 2007

(54) METHODS FOR TREATMENT AND PREVENTION OF NEUROMUSCULAR AND MUSCULAR CONDITIONS BY PERIPHERALLY ADMINISTERED ERYTHROPOIETIN

(75) Inventors: Michael Brines, Woodbridge, CT (US); Anthony Cerami, New York City, NY (US); Carla Cerami, Sleepy Hollow, NY (US)

(73) Assignee: The Kenneth S. Warren Institute, Inc., Ossining, NY (US)

( * ) Notice: Subject to any disclaimer, the term of this patent is extended or adjusted under 35 U.S.C. 154(b) by 0 days.

(21) Appl. No.: 09/717,053

(22) Filed: Nov. 21, 2000

Related U.S. Application Data

(62) Division of application No. 09/547,220, filed on Apr. 11, 2000.

(60) Provisional application No. 60/129,131, filed on Apr. 13, 1999.

(51) Int. Cl.
*A61K 38/18* (2006.01)
(52) U.S. Cl. .................. 514/2; 514/8; 514/12
(58) Field of Classification Search .............. 514/2, 514/8; 530/350, 397
See application file for complete search history.

(56) References Cited

U.S. PATENT DOCUMENTS

| 4,377,513 A | 3/1983 | Sugimoto et al. ......... 26/112 R |
|---|---|---|
| 4,703,008 A | 10/1987 | Lin ........................ 435/240.2 |
| 4,806,524 A | 2/1989 | Kawaguchi et al. ........... 514/8 |
| 4,835,260 A | 5/1989 | Shoemaker ................ 530/397 |
| 5,457,089 A | 10/1995 | Fibi et al. ..................... 514/8 |
| 5,547,933 A | 8/1996 | Lin ............................... 514/8 |
| 5,571,787 A | 11/1996 | O'Brien et al. .............. 514/12 |
| 5,614,184 A | 3/1997 | Sytkowski et al. ......... 424/85.1 |
| 5,618,698 A | 4/1997 | Lin .......................... 435/69.4 |
| 5,621,080 A | 4/1997 | Lin .......................... 530/350 |
| 5,661,125 A | 8/1997 | Strickland ..................... 514/8 |
| 5,696,080 A | 12/1997 | O'Brien ........................ 514/2 |
| 5,700,909 A | 12/1997 | O'Brien ..................... 530/326 |
| 5,714,459 A | 2/1998 | O'Brien ........................ 514/2 |
| 5,756,349 A | 5/1998 | Lin .......................... 435/325 |
| 5,767,078 A | 6/1998 | Johnson et al. .............. 514/12 |
| 5,773,569 A | 6/1998 | Wrighton et al. ........... 530/300 |
| 5,830,851 A | 11/1998 | Wrighton et al. .............. 514/2 |
| 5,835,382 A | 11/1998 | Wilson et al. .............. 364/496 |
| 5,856,298 A | 1/1999 | Strickland ..................... 514/8 |
| 5,888,772 A | 3/1999 | Okasinski et al. ......... 435/69.5 |
| 5,955,422 A | 9/1999 | Lin ............................... 514/8 |
| 6,165,783 A | 12/2000 | Weiss et al. ............... 435/325 |
| 2002/0052309 A1* | 5/2002 | Anagnostou et al. .......... 514/2 |

FOREIGN PATENT DOCUMENTS

| JP | 5-246885 | 9/1993 |
|---|---|---|
| WO | WO95/05465 | 2/1995 |
| WO | WO97/18318 | 5/1997 |
| WO | WO97/32895 | 12/1997 |
| WO | WO98/10650 | * 3/1998 |
| WO | WO98/18926 | 5/1998 |
| WO | WO 00/35475 | 6/2000 |
| WO | WO 01/82952 | 11/2001 |
| WO | WO 01/82953 | 11/2001 |

OTHER PUBLICATIONS

Iseki et al. Increased Risk of Cardiovascular Disease with Erythropoietin in Chronic Dialysis Patients. Nephron 72:30-36 (1996).*
Besarab et al. The Effects of Normal as Compared with Low Hematocrit Values in Patients with Cardiac Disease Who Are receiving Hemodialysis and Epoetin. The New England Journal of Medicine 339/9:584-590 (1998).*
Wit et al. Experimental Models of Ventricular Tachycardia and Fibrillation Caused by Ischemia and Infarction. Circulation 85 Suppl I:I-32-I-42, (1992).*
Bernaudin et al., 1999, "A potential role for erythropoietin in focal permanent cerebral ischemia in mice", J. Cereb. Blood Flow Metab. 19:643-651.
Bondy, 1995, "The relaxation of oxidative stress and hyperexcitation to neurological disease", Proc. Soc. Exp. Biol. Med. 208:337-345.
Brines et al., 2000, "Erythropoietin crosses the blood-brain barrier to -protect against experimental brain injury", Proc. Natl. Acad. Sci. USA 97:10526-10531.
Campana et al., 1998, "Identification of a neurotrophic sequence in erythropoietin", Int. J. Mol. Med. 1:235-241.
Digicaylioglu et al. 1995, "Localization of specific erythropoietin binding sites in defined areas of the mouse brain.", Proc. Natl. Acad. Sci. USA 92:3717-3720.
Dipaolo et al., 1992, "Effects of uremia and dialysis on brain electrophysiology after recombinant erythropoietin treatment", ASAIO J. 38:M477-M480.
Grimm et al., 1990, "Improvement of brain function in hemodialysis patients treated with erythropoietin", Kidney Intl. 38:480-486.
Hefti, 1997, "Pharmacology of neurotrophic factors", Annu. Rev. Pharmacol. Toxicol. 37:239-267.

(Continued)

*Primary Examiner*—Marianne P. Allen
*Assistant Examiner*—Regina M. DeBerry
(74) *Attorney, Agent, or Firm*—Jones Day

(57) ABSTRACT

Methods and compositions are provided for protecting or enhancing excitable tissue function in mammals by systemic administration of an erythropoietin receptor activity modulator, such as erythropoietin, which signals via an EPO-activated receptor to modulate the function of excitable tissue. Excitable tissues include central neuronal tissues, such as the brain, peripheral neuronal tissues, retina, and heart tissue. Protection of excitable tissues provides treatment of hypoxia, seizure disorders, neurodegenerative diseases, hypoglycemia, and neurotoxin poisoning. Enhancement of function is useful in learning and memory. The invention is also directed to compositions and methods for facilitating the transport of molecules across endothelial cell tight junction barriers, such as the blood-brain barrier, by association of molecules with an erythropoietin receptor activity modulator, such as an erythropoietin.

8 Claims, 17 Drawing Sheets

OTHER PUBLICATIONS

Figure 1A:
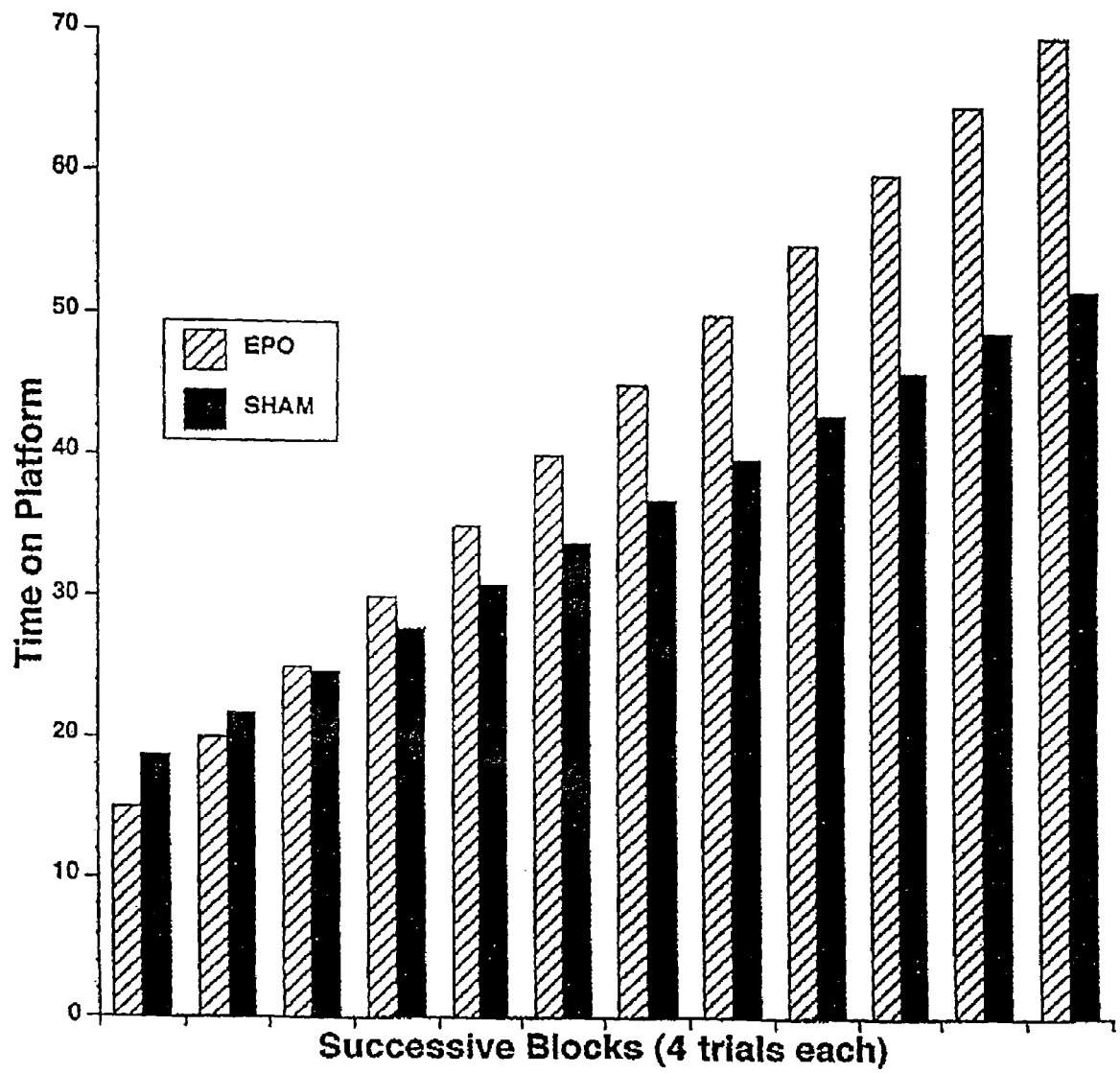

Hengemihle et al., 1996, "Chronic treatment with human recombinant erythropoietin increases hematocrit and improves water maze performance in mice", Physiol. Behav. 59:153-156.

Hirakata et al., 1992, "CBF and oxygen metabolism in hemodialysis patients: effects of anemia correction with recombinant human EPO", Am. J. Physiol. 262:F737-F743.

Juul et al., 1998, "Erythropoietin and erythropoietin receptor in the developing human central nervous system", Pediatr. Res. 43:40-49.

Konishi et al., 1993, "Trophic effect of erythropoietin and other hematopoietic factors on central cholinergic neurons in vitro and in vivo", Brain Res. 609:29-35.

Kopf et al., 1994, "Memory-improving actions of glucose: involvement of a central cholinergic muscarinic mechanism.", Behav. Neural Biol. 62:237-243.

Latini et al., 1998, "Comparative efficacy of a DA2/$\alpha$2 agonist and a $\beta$-blocker in reducing adrenergic drive and cardiac fibrosis in an experimental model of left ventricular dysfunction after coronary artery occlusion", J. Cardiovasc. Pharmacol. 31:601-608.

Li et al., 1998, "A single pre-training glucose injection induces memory facilitation in rodents performing various tasks: contribution of acidic fibroblast growth factor", Neurosci. 85:785-794.

Lipinski et al., 1995, "Nerve growth factor facilitates conditioned taste aversion learning in normal rats", Brain Res. 692:143-153.

Liu et al., 1997, "Regulated human erythropoietin receptor expression in mouse brain", J. Biol. Chem. 272:32395-32400.

Liu et al., 1994, "Tissue specific expression of human erythropoietin receptor in transgenic mice", Devel. Biol. 166:159-169.

Marrero et al., 1998, "Erythropoietin receptor-operated $Ca^{2+}$ channels: activation by phospholipase C-Y1", Kidney Intl. 53:1259-1268.

Marsh et al., 1991, "rHuEPO treatment improves brain and cognitive function of anemic dialysis patients", Kidney Intl. 39:155-163.

Marti et al., 1997, "Detection of erythropoietin in human liquor: intrinsic erythropoietin production in the brain", Kidney Intl. 51:416-418.

Marti et al., 1996, "Erythropoietin gene expression in human, monkey and murine brain", Eur. J. Neurosci. 8:666-676.

Masuda et al., 1997, "Insulin-like growth factors and insulin stimulate erythropoietin production in primary cultured astrocytes", Brain Res. 746:63-70.

Masuda et al., 1994, "A novel site of erythropoietin production. Oxygen-dependent production in cultured rat astrocytes", J. Biol. Chem. 269:19488-19493.

Masuda et al., 1993, "Functional erythropoietin receptor of the cells with neural characteristics. Comparison with receptor properties of erythroid cells", J. Biol. Chem. 268:11208-11216.

Morishita et al., 1997, "Erythropoietin receptor is expressed in rat hippocampal and cerebral cortical neurons, and erythropoietin prevents in vitro glutamate-induced neuronal death", Neurosci. 76:105-116.

Moss and Scholey, 1996, "Oxygen administration enhances memory formation in healthy young adults", Psychopharmacol. 124:255-260.

Nakamura et al., 1998, "Elevated levels of erythropoietin in cerebrospinal fluid of depressed patients", Am. J. Med. Sci. 315:199-201.

Nissenson et al., 1991, "Recombinant human erythropoietin and renal anemia: molecular biology, clinical efficacy and nervous system effects", Ann. Int. Med. 114:402-416.

Nissenson, 1989, "Recombinant human erythropoietin: impact on brain and cognitive function, exercise tolerance, sexual potency and quality of life", Sem. Nephrol. 9(suppl. 2):25-31.

Ogden, 1989, "Monitoring considerations in recombinant human erythropoietin therapy", Sem. Nephrol. 9(suppl. 2):12-15.

Pardridge, 1997, "Drug delivery to the brain", J. Cerebral Blood Flow Metab. 17:713-731.

Pardridge et al., 1991, "Selective transport of an anti-transferrin receptor antibody through the blood-brain barrier in vivo", J. Pharmacol. Exp. Ther. 27:66-70.

Poduslo et al., 1994, "Macromolecular premeability across the blood-nerve and blood-brain barriers", Proc. Natl. Acad. Sci. USA 91:5705-5709.

Prendergast et al., 1997, "Nitric oxide synthase inhibition impairs spatial navigation learning and induces conditioned taste aversion", Pharmacol. Biochem. Behav. 57:347-352.

Rose and Audus, 1998, "Receptor-mediated angiotensin II transcytosis by brain microvessel endothelial cells", Peptides 19:1023-1030.

Sadamoto et al., 1998, "Erythropoietin prevents place navigation disability and cortical infarction in rats with permanent occlusion of the middle cerebral artery", Biochem. Biophys. Res. Comm. 253:26-32.

Sakanaka et al., 1998, "In vivo evidence that erythropoietin protects neurons from ischemic damage", Proc. Natl. Acad. Sci. USA 95:4635-4640.

Tabira et al., 1995, "Neurotrophic effect of hematopoietic cytokines on cholinergic and other neurons in vitro", Int. J. Devl. Neurosci. 13:241-252.

Wolcott et al., 1989, "Recombinant human erythropoietin treatment may improve quality of life and cognitive function in chronic hemodialysis patients", Am. J. Kidney Dis. 14:478-485.

Wu and Pardridge, 1999, "Neuroprotection with noninvasive neurotrophin delivery to the brain", Neurobiol. 96:254-259.

Yamaji et al., 1996, "Brain capillary endothelial cells express two forms of erythropoietin receptor mRNA", Eur. J. Biochem. 239:494-500.

Alafaci et al., 2000, "Effect of Recombinant Human Erythropoietin on Cerebral Ischemia Following Experimental Subarachnoid Hemorrhage," *Eur. J. Phar.*, 406:219-225.

Annable et al., 1972, "The Second International Reference Preparation of Erythropoietin, Human, Urinary, for Bioassay," *Bull. Org. mond. Sante*, 47:99-112.

Ashwell et al., 1978, "A Protein from Mammalian Liver that Specifically Binds Galactose-Terminated Glycoproteins," *Meth. Enzymol.*, 50:287-291.

Bauer, 1995, "The Oxygen Sensor That Controls EPO Production: Facts and Fancies," *J. Perinat. Med.*, 23:7-12.

Briggs et al., 1974, "Hepatic Clearance of Intact and Desialylated Erythropoietin," *Am. J. Physiol.*, 227:1385-1388.

Bruneval et al., 1993, "Erythropoietin Synthesis by Tumor Cells in a Case of Meningioma Associated With Erythrocytosis," *Blood*, 81:1593-1597.

Camiscoli et al., 1968, "Comparative Assay of Erythropoietin Standards," *Annals New York Acad. Sci.*, 149:40-45.

Claus-Walker and Dunn, 1984, "Spinal Cord Injury and Serum Erythropoietin," *Arch. Phys. Med. Rehabil.*, 65:370-374.

Cotes, 1968, "Quantitative Estimation of Erythropoietin," Part I. Assay and Standardization of Erythropoietin, *Annals New York Acad. Sci.*, 149:12-17.

Cotes and Bangham, 1961, "Bio-Assay of Erythropoietin in Mice Made Polycythaemic By Exposure to Air at a Reduced Pressure," *Nature*, 191:1065-1067.

Cotes and Bangham, 1966, "The International Reference Preparation of Erythropoietin," *Bull. Org. mond. Sante*, 35:751-760.

Dordal et al., 1985, "The Role of Carbohydrate in Erythropoietin Action," *Endocrinol.*, 116:2293-2299.

Dube et al, 1988, "Glycosylation at Specific Sites of Erythropoietin is Essential for Biosynthesis, Secretion, and Biological Function," *J. Biol. Chem.*, 263:17516-17521.

*Eur. Pharmacopoeia*, 1997, p. 5.

*Eur. Pharmacopoeia, Suppl.* 2001, pp. 777-782.

Fukuda et al., 1989, "Survival of Recombinant Erythropoietin in the Circulation: The Role of Carbohydrates," *Blood*, 73:84-89.

Garthoff, 1995, "Safety and Efficacy Testing of Hormones and Related Products," The Report and Recommendations of ECVAM Workshop 9, *A.T.L.A.*, 23:699-711.

Goldwasser et al., 1974, "On the Mechanism of Erythropoietin-Induced Differentiation," XIII. The Role of Sialic Acid in Erythropoietin Action, *J. Biol. Chem.*, 249:4202-4206.

Goldwasser et al., 1975, "An Assay for Erythropoietin in Vitro at the Milliunit Level," *Endo.*, 97:315-323.

Goldwasser and Gross, "Erythropoietin: Assay and Study of Its Mode of Action," *Hormone Assays*, pp. 109-121, 1975.

Hammond et al., 1968, "Production, Utilization and Excretion of Erythropoietin: I. Chronic Anemias. II. Aplastic Crisis. III. Erythropoietic Effects of Normal Plasma," *Erythropoietin*, 149:516-527.

Horton et al., 1991, "Von Hippel-Lindau Disease and Erythrocytosis: Radioimmunoassay of Erythropoietin in Cyst Fluid From a Brainstem Hemangioblastoma," *Neurology*, 41:753-754.

Imai et al., 1990, "Physicochemical and Biological Characterization of Asialoerythropoietin," *Eur. J. Biochem.*, 194:457-462.

Keighley, 1968, "Further Experiences with Assays, Units, and Standards of Erythropoietin," *Annals New York Acad. Sci.*, 149:18-24.

Kohama et al., 2000, "Large Uterine Myoma with Erythropoietin Messenger RNA and Erythrocytosis," *Obstetrics and Gynecology*, 96:826-828.

Lowy et al., 1960, "Inactivation of Erythropoietin by Neuraminidase and by Mild Substitution Reactions," *Nature*, 185:102-103.

Matsuyama et al., 2000, "Erythrocytosis Caused by an Erythropoietin-Producing Hepatocellular Carcinoma," *J. Surg. Oncology*, 75:197-202.

Miyake et al., 1977, "Purification of Human Erythropoietin," *J. Biol. Chem.*, 252:5558-5564.

Morrell et al., 1968, "Physical and Chemical Studies on Ceruloplasmin," Metabolic Studies on Sialic Acid-Free Ceruloplasmin In Vivo, *J. Biol. Chem.*, 243:155-159.

Nakamura et al., 1998, "Elevated Levels of Erythropoietin in Cerebrospinal Fluid of Depressed Patients," *Am. J. Med. Sci.*, 315:199-201.

Shiramizu et al., 1994, "Constitutive Secretion of Erythropoietin by Human Renal Adenocarcinoma Cells in Vivo and in Vitro," *Exp. Cell Res.*, 215:249-256.

Shore et al., 1968, "Quantitative Estimation of Erythropoietin," *Annals New York Acad. Sci.*, 149:46-48.

Spivak and Hogans, 1989, "The In Vivo Metabolism of Recombinant Human Erythropoietin in the Rat," *Blood*, 73:90-99.

Storring et al., 1998, "Epoietin Alfa and Beta Differ In Erythropoietin Isoform Compositions and Biological Properties," *British J. Haematology*, 100:79-89.

Storring and Gaines Das, 1992, "The International Standard for Recombinant DNA-Derived Erythropoietin: Collaborative Study of Four Recombinant DNA-derived Erythropoietins and Two Highly Purified Human Urinary Erythropoietins," *J. Endocrinol.*, 134:459-484.

Suzuki et al., 2001, "Erythropoietin Synthesis by Tumour Tissues in a Patient With Uterine Myoma and ERythrocytosis," *British J. Haematology*, 113:49-51.

Weiland et al., "In vivo Activity of Asialo-Erythropoietin in Combination with Asialo-Glycoproteins," 1982, *Blut*, 44:173-175.

Cardin S et al. 2003, Evolution of the atrial fibrillation substrate in experimental congestive heart failure: angiotensin-dependent and -independent pathways. Cardiovasc Res. 60(2): 315-325.

Dispersyn GD et al. 1999, Cardiomyocyte remodelling during myocardial hibernation and atrial fibrillation: prelude to apoptosis. Cardiovasc Res. 43(4): 947-957.

Fishbein MC et al. 1981, Early phase acute myocardial infarct size quantification: validation of the triphenyl tetrazolium chloride tissue enzyme staining technique. Am Heart J. 101(5): 593-600.

Greenberg HE et al. 1995, Congestive heart failure and sleep apnoea-possible mechanisms and effect of CPAP therapy. J Sleep Res. 4(S1): 130-134.

Kaye DM et al., 2003, Feasibility and short-term efficacy of percutaneous mitral annular reduction for the therapy of heart failure-induced mitral regurgitation. Circulation. 108(15): 1795-1797.

Lee P et al. 1998, Conditional lineage ablation to model human diseases. Proc Natl Acad Sci U S A. 95(19): 11371-11376.

Opitz CF et al. 1995, Arrythmias and death after coronary artery occlusion in the rat. Continuous telemetric ECG monitoring in conscious, untethered rats. Circulation. 92(2):253-261.

Opitz CF et al. 1998, Effects of reperfusion on arrythmias and death after coronary artery occlusion in the rat: increased electrical stability independent of myocardial salvage. J Am Coll Cardiol. 32(1): 261-267.

Pfeffer JM et al. 1991, Progressive ventricular remodeling in rat with myocardial infarction. Am J Physiol. 260(5 Pt 2): H1406-1414.

Teien DE et al., 1995, Doppler evaluation of severity of mitral regurgitation: relation to pulmonary venous blood flow patterns in an animal study. J Am Coll Cardiol. 25(1): 264-268.

Xiao Q et al. 1998, Fibrinogen deficiency is compatible with the development of atherosclerosis in mice. J Clin Invest. 101(5): 1184-1194.

Spivak and Hogans, 1989, "The in vivo metabolism of recombinant human erythropoietin in the rat", Blood 73:90-99.

Wojchowski and Caslake, 1989, "Biotinylated recombinant human erythropoietins: bioactivity and utility as receptor ligand", Blood 74:952-958.

Ehrenreich et al., 2002, "Erythropoietin therapy for acute stroke is both safe and beneficial," Molec. Med. 8:495-505.

Bianchi et al., 2004, "Erythropoietin both protects from and reverses experimental diabetic neuropathy," PNAS 101:823-828.

Agnello et al., 2002, "Erythropoietin exerts an anti-inflammatory effect on the CNS in a model of experimental autoimmune encephalomyelitis," Brain Research 952:128-134.

Bogoyevitch, 2004, "An update on the cardiac effects of erythropoietin cardioprotection by erythropoietin and the lessons learnt from studies in neuroprotection," Cardiovascular Research 63:208-216.

van der Meer, Erythropoietin Induces Neovascularization and Improves Cardiac Function in Rats with Heart Failure After Myocardial Infarction, JACC, 2005, 125-33, 46(1).

Abdelrahman, Erythropoietin Attenuates the Tissue Injury Associated with Hemorrhagic Shock an Myocardial Ischemia, SHOCK, 2004, 63-69, 22(1).

Emir, Effect of Erythropoietin on bcl-2 Gene Expression in Rat Cardiac Myocytes After Traumatic Brain Injury, Transplantation Proceedings, 2004, 2935-2938, 36.

Mitsuma et al., Biochemical and Biophysical Research Communications, 2006, 987-994, 344.

Anagnostou et al., 1994, "Erythropoietin receptor mRNA expression in human endothelial cells", Proc. Natl. Acad. Sci. USA 91:3974-3978.

Benyo and Conrad, 1999, "Expression of erythropoietin receptor by trophoblast cells in the human placenta", Biol. Reproduct. 60:861-870.

Bernaudin et al., 2000, Neurons and astrocytes express EPO mRNA: oxygen-sensing mechanism that involve the redox-state of the brain, Glia 30271-278.

Ehrenreich et al., 2002, "Erythropoietin therapy for acute stroke is both safe and beneficial", Molec. Med., in press.

Farrell et al., 2001, "Erythropoietin crosses the blood brain barrier", Blood 98:148b (abstr. #4265; 43rd Annual Meeting of the American Society of Hematology, Orlando FL, Dec. 7-11, 2001).

Gorio et al., 2002, "Recombinant human erythropoietin counteracts secondary injury and markedly enhances neurological recovery from experimental spinal cord trauma", Proc. Natl. Acad. Sci. USA 99 ;9450-9455 (PNAS Early Edition www.pnas.org/cgi/doi/10.1073/pnas.142287899).

Grasso et al., 2002, "Beneficial effects of systemic administration of recombinant human erythrpoietin in rabbits subjected to subarachnoid hemorrhage", Proc. Natl. Acad. Sci. USA 99:5627-5631.

Gregory et al., 1999, "GATA-1 and erythropoietin cooperate to promote erythroid cell survival by regulating bci-$x_L$ expression", Blood 94:87-96.

Junk et al., 2002, "Erythropoietin administration protects retinal neurons from acute ischemia-reperfusion injury", Proc. Natl. Acad. Sci. USA 99:10659-10664 (PNAS Early Edition www.pnas.org/cgi/doi/10.1073/pnas.152321399).

Juul et al., 2001, "Recombinant erythropoietin (EPO) crosses the blood brain barrier (BBB) in preterm fetal sheep", Soc. for Neuroscience Abstracts 27:929 (31st Annual Meeting of the Society for Neuroscienc, San Diego, CA Nov. 10-15, 2001).

Juul et al., 1998, "Tissue distribution of erythropoietin and erythropoietin receptor in the developing human fetus", Early Human Devel. 52:235-249.

Li et al., 1996, "Erythropoietin receptors are expressed in the central nervous system of mid-trimester human fetuses", Pediatr. res. 40:376-380.

Liu et al., 1996, "Transgenic mice containing the human erythropoietin receptor gene exhibit correct hematopoietic and neural expression", Proc. Assoc. Am. Physicians 108:449-454.

Mioni et al., 1992, "Evidence for specific binding and stimulatory effects of recombinant human erythropoietin on isolated adult rat Leydig cells", Acta Endocrinologica 127:459-465.

Okada et al., 1996, "Erythropoietin stimulates proliferation of rat-cultured gastric mucosal cells", Digestion 57:328-332.

Sawyer et al., 1989, "Receptors for erythropoietin in mouse and human erythroid cells and placenta", Blood 74:103-109.

Silva et al., 1999, "Erythropoietin can induce the expression of bcl-$x_L$ through stat5 in erythropoietin-dependent progenitor cell lines", J. Biol. Chem. 274:22165-22169.

Sirén et al., 2001, "Erythropoietin prevents neuronal apoptosis after cerebral ischemia and metabolic stress", Proc. Natl. Acad. Sci. USA 98:4044-4049.

Westenfelder et al., 1999, "Human, rat and mouse kidney cells express functional erythropoietin receptors", Kidney Intl. 55:808-820.

Williams et al., 1994, "Human erythropoietin receptor", Ann. NY Acad. Sci. 718:232-244.

* cited by examiner

METHODS FOR TREATMENT AND PREVENTION OF NEUROMUSCULAR AND MUSCULAR CONDITIONS BY PERIPHERALLY ADMINISTERED ERYTHROPOIETIN

This is a division of application Ser. No. 09/547,220, filed Apr. 11, 2000, now abandoned, which the entire contents of which are incorporated herein by reference in its entirety.

This application is a divisional of application Ser. No. 09/547,220, filed Apr. 11, 2000, now abandoned, which claims priority under 35 U.S.C. §119(e) to U.S. provisional patent Application No. 60/129,131 filed Apr. 13, 1999, the entire contents of each of which is incorporated herein by reference in its entirety.

1. FIELD OF THE INVENTION

The present invention is directed to the use of peripherally administered erythropoietin and other erythropoietin receptor activity modulators or EPO-activated receptor modulators to positively affect excitable tissue function. This includes the protection of excitable tissue, such as neuronal and cardiac tissue, from neurotoxins, hypoxia, and other adverse stimuli, and the enhancement of excitable tissue function, such as for facilitating learning and memory. The present invention is further drawn to methods for transport of substances across endothelial cell barriers by association with an erythropoietin molecule, erythropoietin receptor activity modulator or other EPO-activated receptor modulators.

2. BACKGROUND OF THE INVENTION

Various acute and chronic conditions and diseases originate from excitable tissue damage and dysfunction brought about by external and internal stimuli. Such stimuli include lack of adequate oxygenation or glucose, neurotoxins, consequences of aging, infectious agents, and trauma. For example, excitable tissue may be subjected to damage as a consequence of seizures and chronic seizure disorders, convulsions, epilepsy, stroke, Alzheimer's disease, Parkinson's disease, central nervous system injury, hypoxia, cerebral palsy, brain or spinal cord trauma, ADS dementia and other forms of dementia, age-related loss of cognitive function, memory loss, amyotrophic lateral sclerosis, multiple sclerosis, hypotension, cardiac arrest, neuronal loss, smoke inhalation and carbon monoxide poisoning.

It is widely understood that decreases in energy supply available to the brain, such as glucose or oxygen, results in a profound impairment of brain function, including cognition. Many (but not all) neurons in the central nervous system are easily damaged while working under metabolically-limited conditions, e.g., hypoxia, hypoglycemia, stress, and/or prolonged, strong excitation. Under these circumstances, the electrochemical gradients of these cells often collapse, resulting in irreversible neuronal injury and cell death. Current opinion favors this general mechanism as a common final pathway for a wide range of common and debilitating degenerative neurological diseases including stroke, epilepsy, and Alzheimer's disease.

Although the consequences of limited energy substrate on brain function are well known, the effects of improving energy delivery in an otherwise normal brain has been less extensively explored. Current data suggest strongly that improved delivery of either glucose or oxygen markedly improves complex cognitive function in both animal models and in normal human subjects (Kopf et al., 1994, Behavioral and Neural Biology 62:237-243; Li et al., 1998, Neuroscience 85:785-794; Moss et al., 1996, Psychopharmacology 124:255-260). Further, a growing list of neuropeptides produced within the brain have been demonstrated to directly provide an improvement in cognitive function in normal brain. The physiological basis of these enhancements ultimately depends upon remodeling of neuronal interconnections through synaptic changes.

Brain tissue cytoarchitecture exhibits extreme plasticity and undergoes continuous remodeling. These processes, mediated by many trophic molecules, occur not only following injury, but also play a prominent role in learning, memory, and cognitive function. Although the prototype neurotrophin is nerve growth factor (NGF), an increasing number of cytokines have been recognized to perform trophic functions in the brain (Hefti et al. 1997, Annu. Rev. Pharmacol. Toxicol. 37:239-67).

Recently, a number of independent investigators have recognized that nervous tissue expresses high levels of both EPO and its receptor (EPO-R; Digicaylioglu et al., 1998, Proc. Natl. Acad. Sci. USA 92:3717-20; Juul et al., Pediatr. Res. 43:40-9; Marti et al., 1997, Kidney Int. 51:416-8; Morishita et al., 1997, Neuroscience 76:105-16). Although it appears that EPO and its receptor proteins are each the products of single genes, the CNS versions are significantly smaller. The physiological meaning of this observation has not been clarified, but the mass differences do appear to modify biological activity. For example, in studies of human patients, investigators have concluded that EPO is not transported into the brain from the periphery (Marti et al., 1997, supra). To date, however, this possibility has not been evaluated for EPO by any direct study. Although brain EPO is about 15% smaller than renal EPO (due to differences in sialylation), brain EPO is more active in erythroid colony stimulation at low ligand concentrations (Masuda et al., 1994, J. Biol. Chem. 269:19488-93). On the other hand, the CNS receptor exhibits a much lower affinity for deglycosylated EPO than the 30% larger peripheral receptor (Konishi et al., 1993, Brain Res. 609:29-35; (Masuda et al., 1993, J. Biol. Chem. 268:11208-16).

In the brain, EPO expression has been found in astrocytes, and increased EPO expression and release can be induced by hypoxia and other metabolic stressors (Marti et al., 1996, Eur. J. Neurosci. 8:666-76; Masuda et al., 1993, J. Biol. Chem. 268:11208-16; Masuda et al., 1994, J. Biol. Chem. 269:19488-93) or even by occupancy of other receptors such as insulin-like growth factor family (Masuda et al., 1997, Brain Res. 746:63-70). Neurons are one target for this secreted EPO as they express EPO-R in a highly cell type-specific manner (Morishita et al., 1997, Neuroscience 76:105-16). In contrast to EPO itself, EPO-R density does not appear to be modulated during metabolic stress (Digicaylioglu et al., 1995, Proc. Natl. Acad. Sci. USA 92:3717-20).

Recent study has demonstrated that EPO impressively protects against hypoxic neuronal injury in vitro, as well as in vivo when injected directly into the cerebral ventricles (Morishita et al., 1997, Neuroscience 76:105-16; Sadamoto et al., 1998, Biochem. Biophys. Res. Commun. 253:26-32; Sakanaka et al., 1998, Proc. Natl. Acad. Sci. USA 95:4635-40). Konishi et al. (1993, Brain Res. 609:29-35) have demonstrated that EPO promotes the in vivo survival of cholinergic neurons in adult rats when injected directly into the cerebral ventricles. EPO administered centrally into the cerebral ventricles also successfully prevents ischemic injury-related deficits in spatial learning in rats (Sadamoto et al., 1998, Biochem. Biophys. Res. Commun. 253:26-32). A recent publication suggests that only a 17-amino acid portion of EPO is needed for these neurotrophic effects in cultured neural cells (Campana et al., 1998, Int. J. Mol. Med. 1:235-41).

For many years, the only clear physiological role of erythropoietin (EPO) had been its control of the production of red blood cells. Recently, several lines of evidence suggest that EPO, as a member of the cytokine superfamily, performs other important physiologic functions which are mediated through interaction with the erythropoietin receptor (EPO-R). These actions include mitogenesis, modulation of calcium influx into smooth muscle and neural cells, and effects on intermediary metabolism. It is believed that EPO provides compensatory responses that serve to improve hypoxic cellular microenvironments. Although studies have established that EPO injected intracranially protects neurons against hypoxic neuronal injury, intracranial administration is an impractical and unacceptable route of administration for therapeutic use, particularly for normal individuals. Furthermore, previous studies of anemic patients given EPO have concluded that peripherally-administered EPO is not transported into the brain (Marti et al., 1997, supra).

Citation or discussion of a reference herein shall not be construed as an admission that such is prior art to the present invention.

3. BRIEF SUMMARY OF THE INVENTION

The present invention is directed to compositions and methods for modulating excitable tissue function in mammals, as well as methods and compositions for drug delivery to excitable tissues. The invention is based, in part, on the Applicants' discovery that erythropoietin (EPO), administered systemically and at a high dosage, is specifically taken up by the brain. In particular, the Applicants have found that EPO, delivered in high doses, can cross the blood-brain barrier, where it can enhance cognitive function, and protect neural tissue from damage resulting from stressful conditions, such as hypoxia.

Erythropoietin and EPO, used interchangeably herein, and EPO receptor activity modulators, and EPO-activated receptor modulators refer to compounds, which, when administered systemically (outside the blood-brain barrier), are capable of activating EPO-activated receptors of electrically excitable tissues to enhance and/or protect from injury and death. Thus, EPO can refer to any form of erythropoietin that can modulate excitable tissue, as well as EPO analogs, fragments and mimetics thereof. In a preferred embodiment, for use in the methods of the present invention, the erythropoietin displays increased specificity for the brain EPO receptor. In another embodiment, the erythropoietin is nonerythropoietic. In yet another embodiment, the erythropoietin is administered at a dose greater than the dose necessary to maximally stimulate erythropoiesis.

The present invention provides a pharmaceutical composition in dosage unit form adapted for modulation of excitable tissue, enhancement of cognitive function or delivery of compounds across endothelial tight junctions which comprises, per dosage unit, an effective non-toxic amount within the range from about 50,000 to 500,000 Units of EPO, an EPO receptor activity modulator, an EPO-activated receptor modulator, or a combination thereof, and a pharmaceutically acceptable carrier. In one embodiment, the effective non-toxic amount of EPO in said pharmaceutical composition comprises 50,000 to 500,000 Units of EPO. In another embodiment, the effective non-toxic amount of EPO of said pharmaceutical preparation is a dose effective to achieve a circulating level of EPO of greater than 10,000 mU/ml of serum. In another embodiment, the circulating level of EPO is achieved about 1, 2, 3, 4, 5, 6, 7, 8, 9, or 10 hours after the administration of EPO. In another embodiment, the invention provides a pharmaceutical kit comprising an effective amount of EPO for modulation of excitable tissue, enhancement of cognitive function or delivery of compounds across endothelial tight junctions packaged in one or more containers.

The present invention provides a method for modulating the function of excitable tissue in a mammal, comprising administering peripherally to said mammal an effective amount of an erythropoietin. The excitable tissue may be normal tissue or abnormal, diseased tissue. In one embodiment, the excitable tissue is neuronal tissue of the central nervous system. In other embodiments, the excitable tissue is selected from the group consisting of neuronal tissue of the peripheral nervous system and heart tissue.

In one embodiment, a method is provided for the enhancement of excitable tissue function in a mammal, in particular, both normal and abnormal, excitable tissue, by administering peripherally an effective amount of EPO or an EPO receptor activity modulator. Enhancement of excitable tissue function provides enhancement of, for example, learning, associative learning, or memory. Non-limiting examples of conditions or diseases treatable by this aspect of the present invention include mood disorders, anxiety disorders, depression, autism, attention deficit hyperactivity disorder, Alzheimer's disease, aging and cognitive dysfunction.

In another embodiment, the modulation of excitable tissue provides protection from pathology resulting from injury to excitable tissue, for example, to neurons of the central nervous system, peripheral nervous system, or heart tissue. Such pathology may result from injuries including, but not limited to hypoxia, seizure disorders, neurodegenerative diseases, neurotoxin poisoning, multiple sclerosis, hypotension, cardiac arrest, radiation, or hypoglycemia. In one embodiment, the pathology is a result of hypoxia, and may be prenatal or postnatal oxygen deprivation, suffocation, choking, near drowning, post-surgical cognitive dysfunction, carbon monoxide poisoning, smoke inhalation, chronic obstructive pulmonary disease, emphysema, adult respiratory distress syndrome, hypotensive shock, septic shock, insulin shock, anaphylactic shock, sickle cell crisis, cardiac arrest, dysrhythmia or nitrogen narcosis. In the instance wherein the pathology is a seizure disorder, it may be, by way of non-limiting example, epilepsy, convulsions or chronic seizure disorder. In the instance wherein the pathology is a neurodegenerative disease, it may be, for example, stroke, Alzheimer's disease, Parkinson's disease, cerebral palsy, brain or spinal cord trauma, AIDS dementia, age-related loss of cognitive function, memory loss, amyotrophic lateral sclerosis, seizure disorders, alcoholism, retinal ischemia, aging, glaucoma or neuronal loss. In another embodiment, administration of EPO may be used to prevent injury or tissue damage during surgical procedures, such as, for example, tumor resection or aneurysm repair.

In yet another embodiment, methods are provided for facilitating the transcytosis of a molecule across an endothelial cell barrier in a mammal by administration of a composition of a molecule in association with erythropoietin. The association between the molecule to be transported and EPO may be, for example, a labile covalent bond, a stable covalent bond, or a noncovalent association with a binding site for the molecule. In one embodiment, the endothelial cell barriers may be the blood-brain barrier, the blood-eye barrier, the blood-testes barrier, the blood-ovary barrier or the blood-placenta barrier.

The invention further provides a composition for transporting a molecule via transcytosis across an endothelial cell barrier comprising said molecule in association with an EPO, an EPO receptor activity modulator, or an EPO-activated receptor modulator. In one embodiment, the EPO is erythropoietin, an erythropoietin analog, an erythropoietin mimetic, an erythropoietin fragment, a hybrid erythropoietin molecule, an erythropoietin receptor-binding molecule, an erythropoietin agonist, a renal erythropoietin, a brain erythropoietin, an oligomer thereof, a multimer thereof, a mutein thereof, a congener thereof, a naturally-occurring form thereof, a synthetic form thereof, a recombinant form thereof, or a combination thereof. In another embodiment, the molecule of said composition is a hormone, a neurotrophic factor, an antimicrobial agent, a radiopharmaceutical, an antisense compound, an antibody, an immunosuppressant, a toxin, or an anti-cancer agent.

Suitable molecules for transport by the method of the present invention include, but are not limited to hormones, such as growth hormone, antibiotics, anti-cancer agents, and toxins.

These and other aspects of the present invention will be better appreciated by reference to the following Figures and Detailed Description.

4. BRIEF DESCRIPTION OF THE FIGURES

Figure 1B:
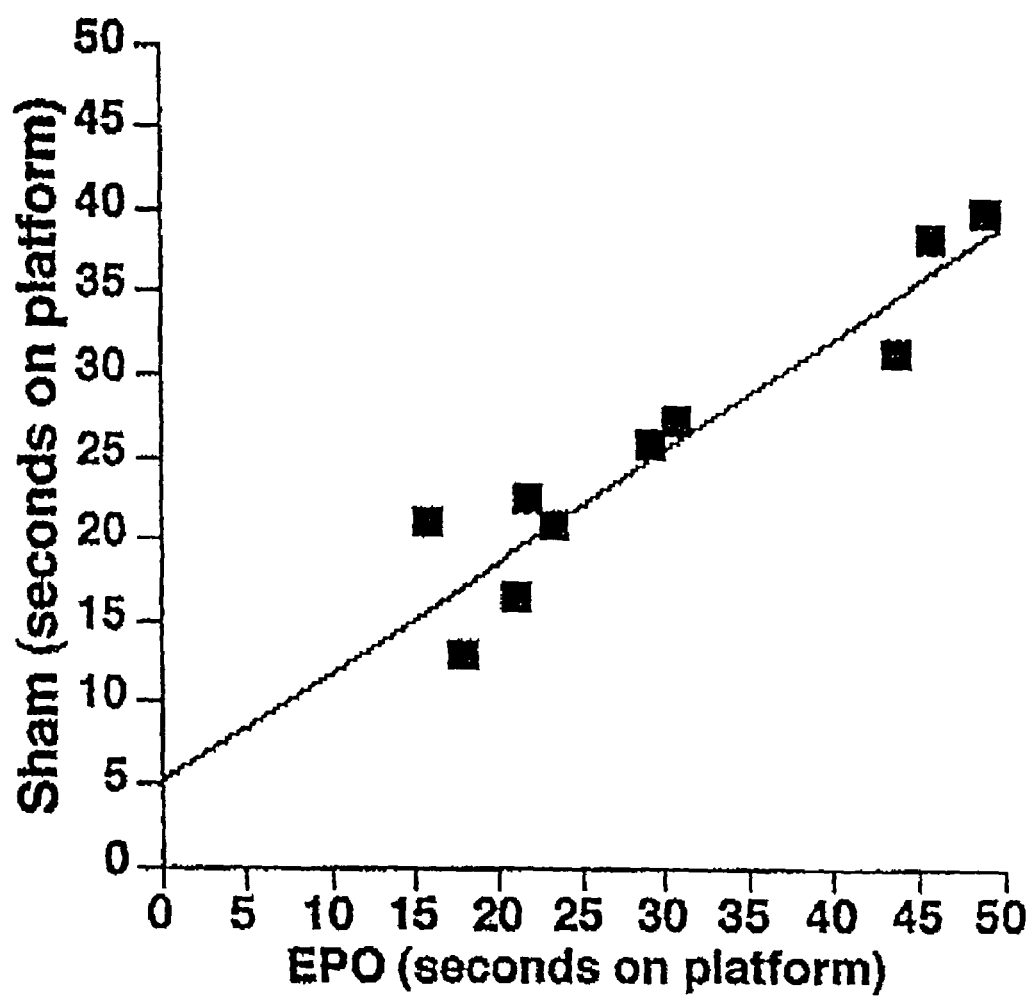

FIGS. 1A-B. Morris Water Maze test A. The results of a Morris Water Maze test performed in mice receiving either EPO or saline (SHAM) administered peripherally each day. B. Subjects receiving EPO performed significantly better than SHAM treated subjects. The regression line ($R^2=0.88$) shows a slope (0.68) significantly different from a slope of 1, markedly in favor of the EPO group.

Figure 2A:
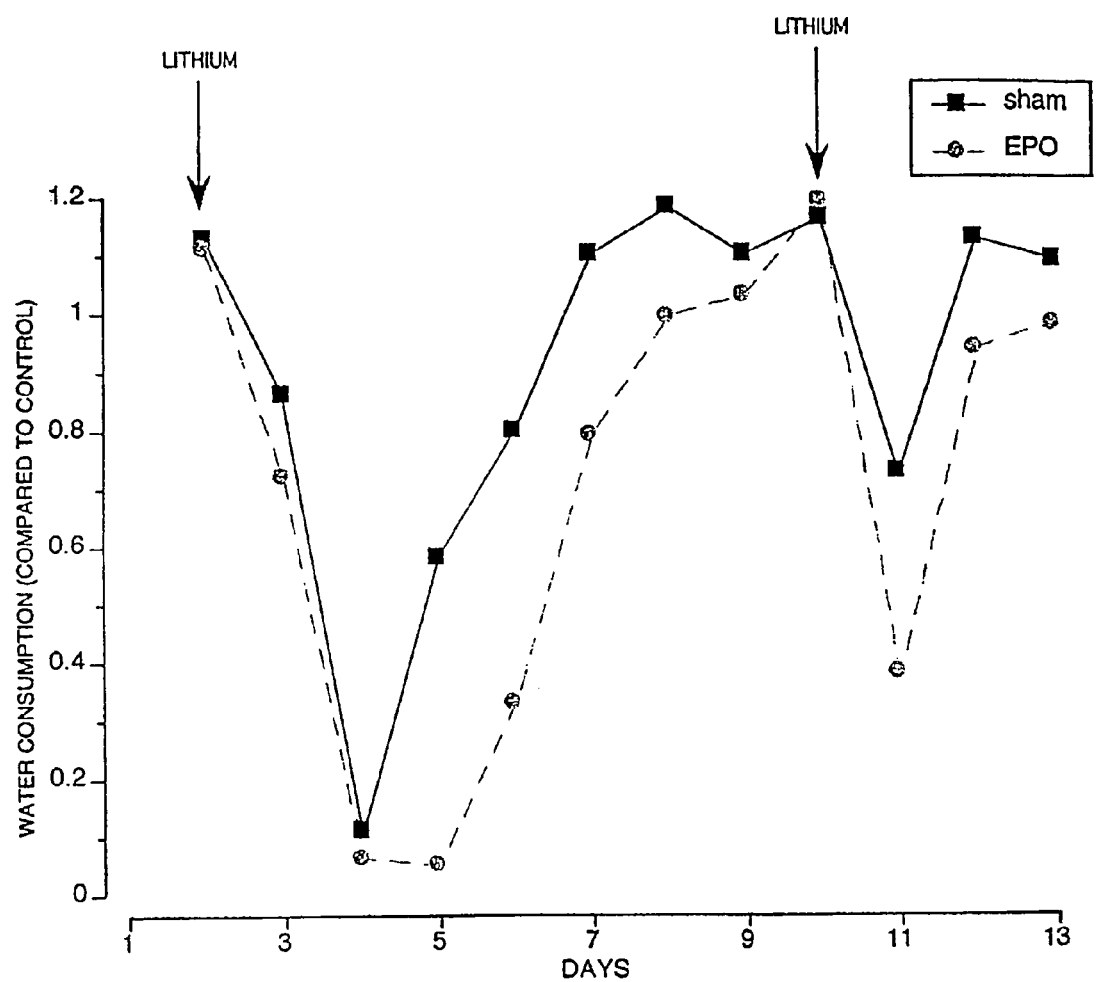
Figure 2B:
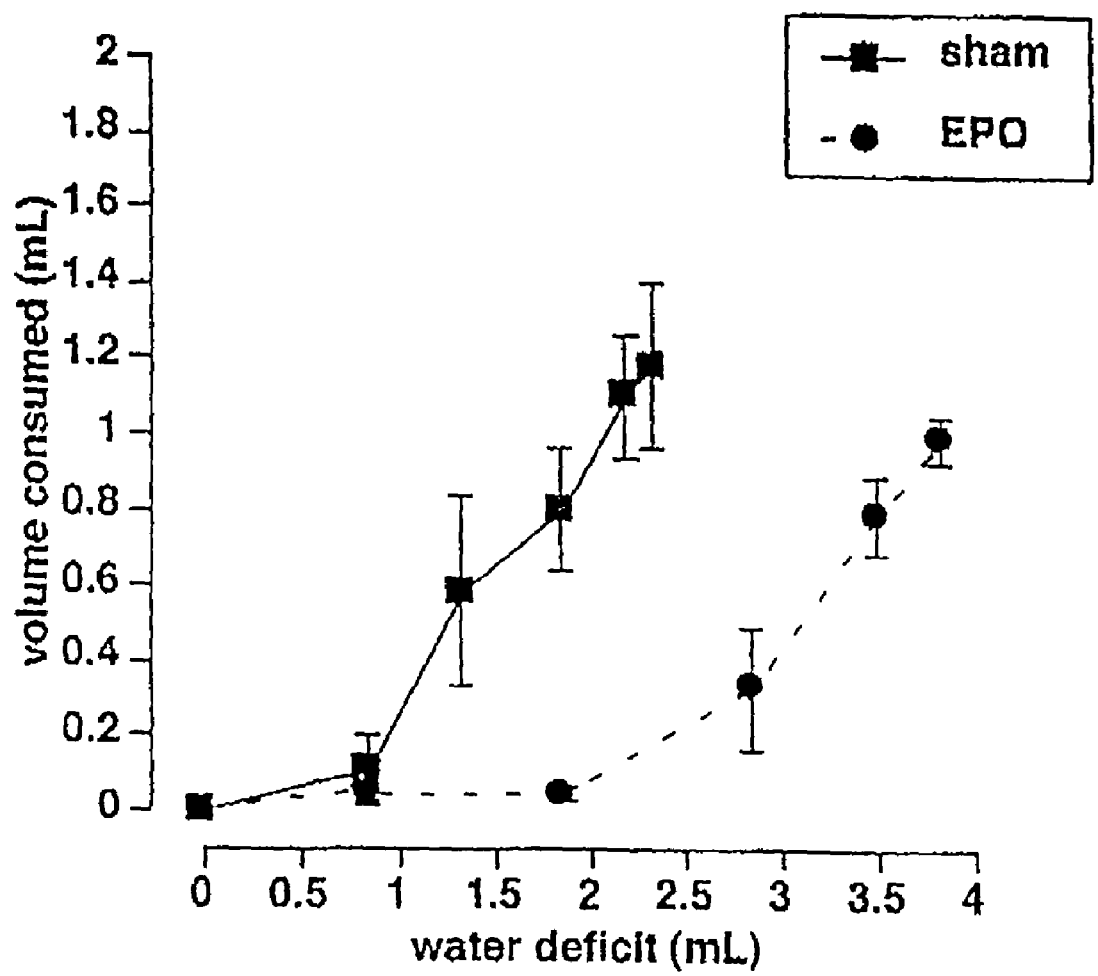
Figure 2C:
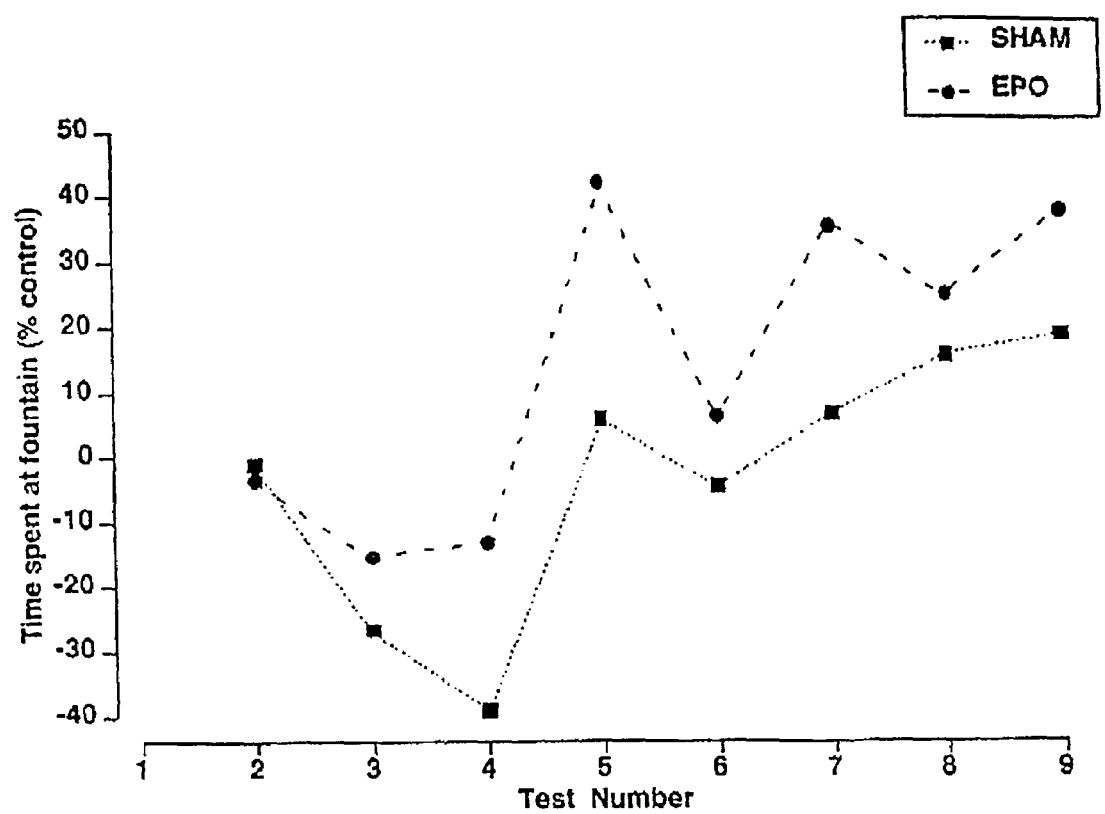

FIGS. 2A-C. Conditioned Taste Aversion test A. Comparison of peripheral sham and EPO treatment on water consumption in mice undergoing Conditioned Taste Aversion testing. Water consumption is expressed as a percentage of the volume consumed by control mice, which were not made ill with lithium chloride. B and C illustrate that the EPO-enhanced learning is robust, as EPO subjects tolerated much greater thirst than controls in avoidance of water containing the illness-associated cue yet spent more time seeking water.

Figure 3A:
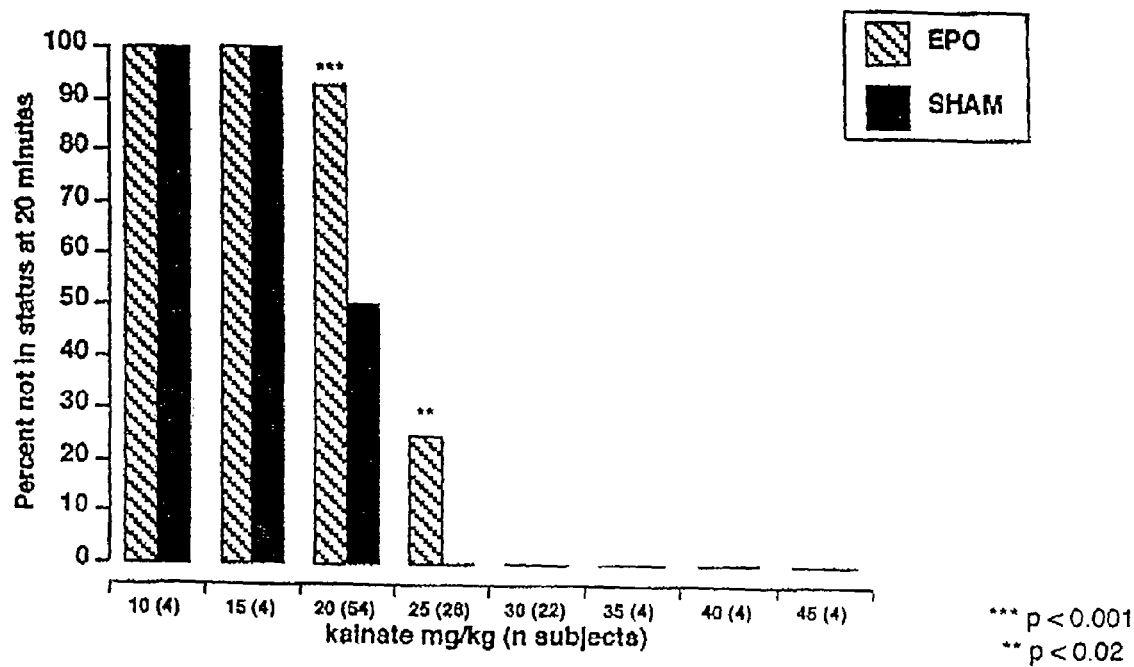
Figure 3B:
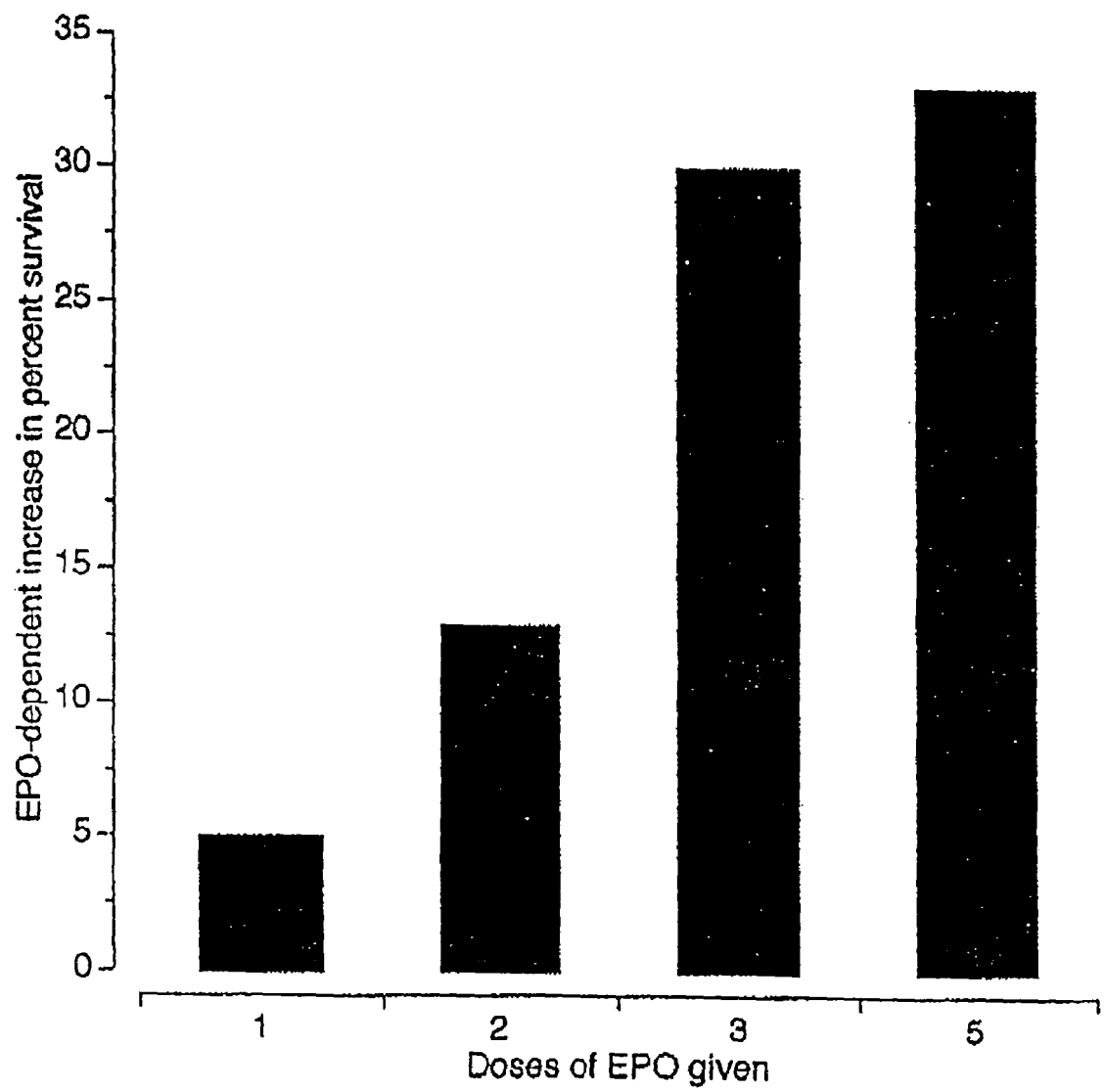
Figure 3C:
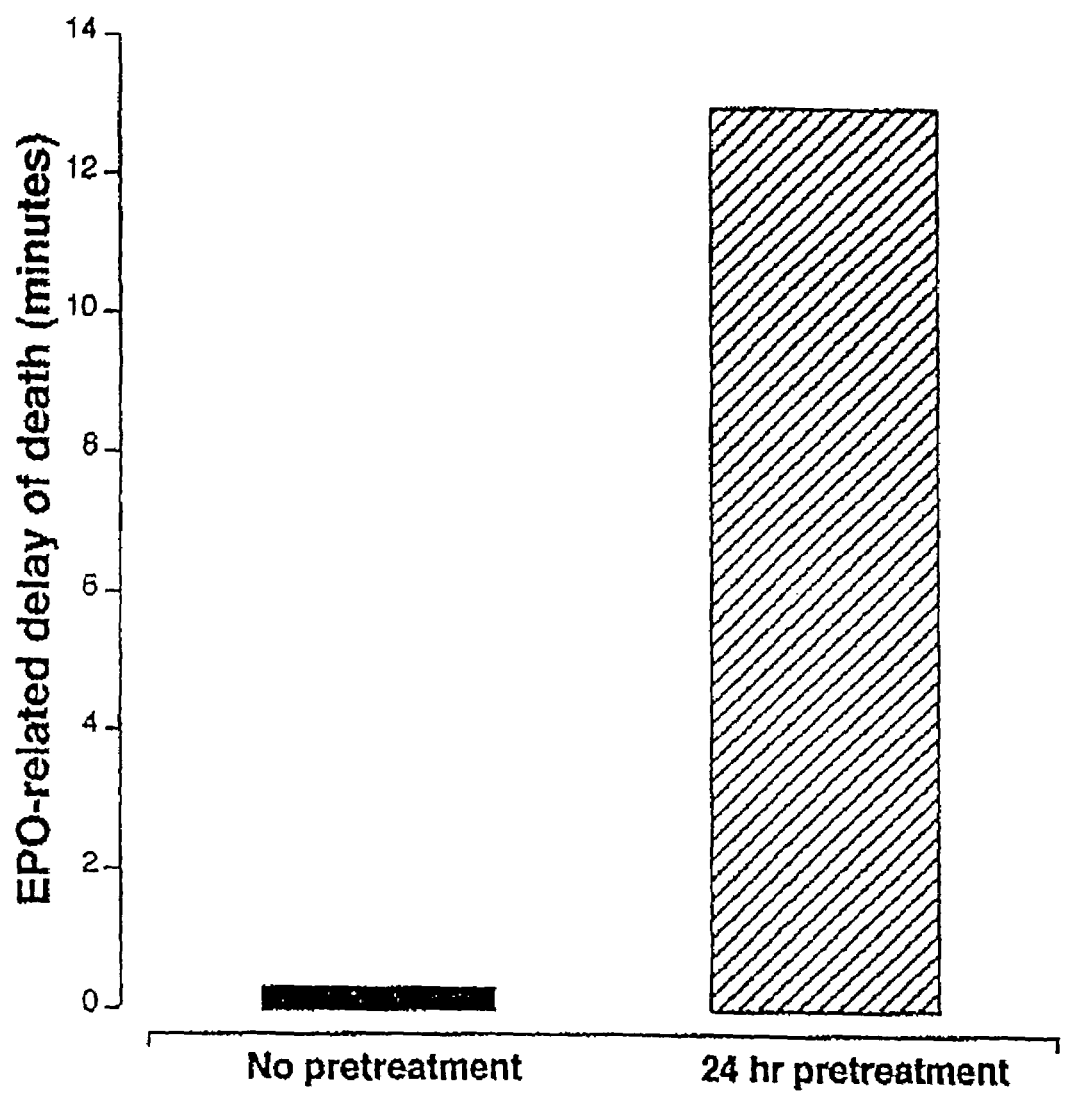

FIGS. 3A-C. A. The results of an experiment which demonstrates that peripherally-administered EPO pretreatment reduces seizure severity and protects mice from convulsions and death by the neurotoxin kainate. The numbers in parentheses under each column indicate the number of animals receiving each kainate dose. B shows that the protective effects of peripherally-administered EPO increase with daily administration of EPO. C illustrates that the onset of action of EPO is delayed, characteristic of the induction of a gene expression program.

Figure 4A:
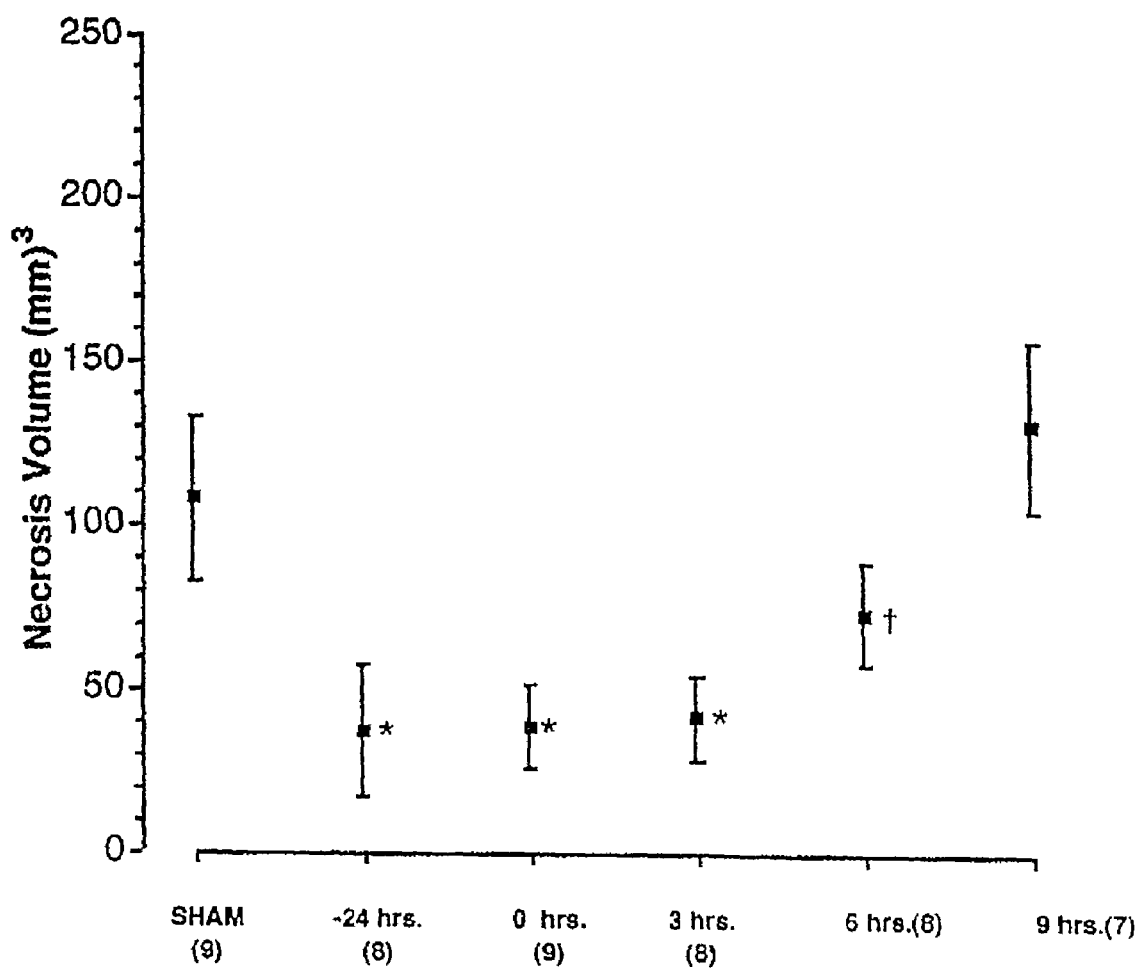
Figure 4B:
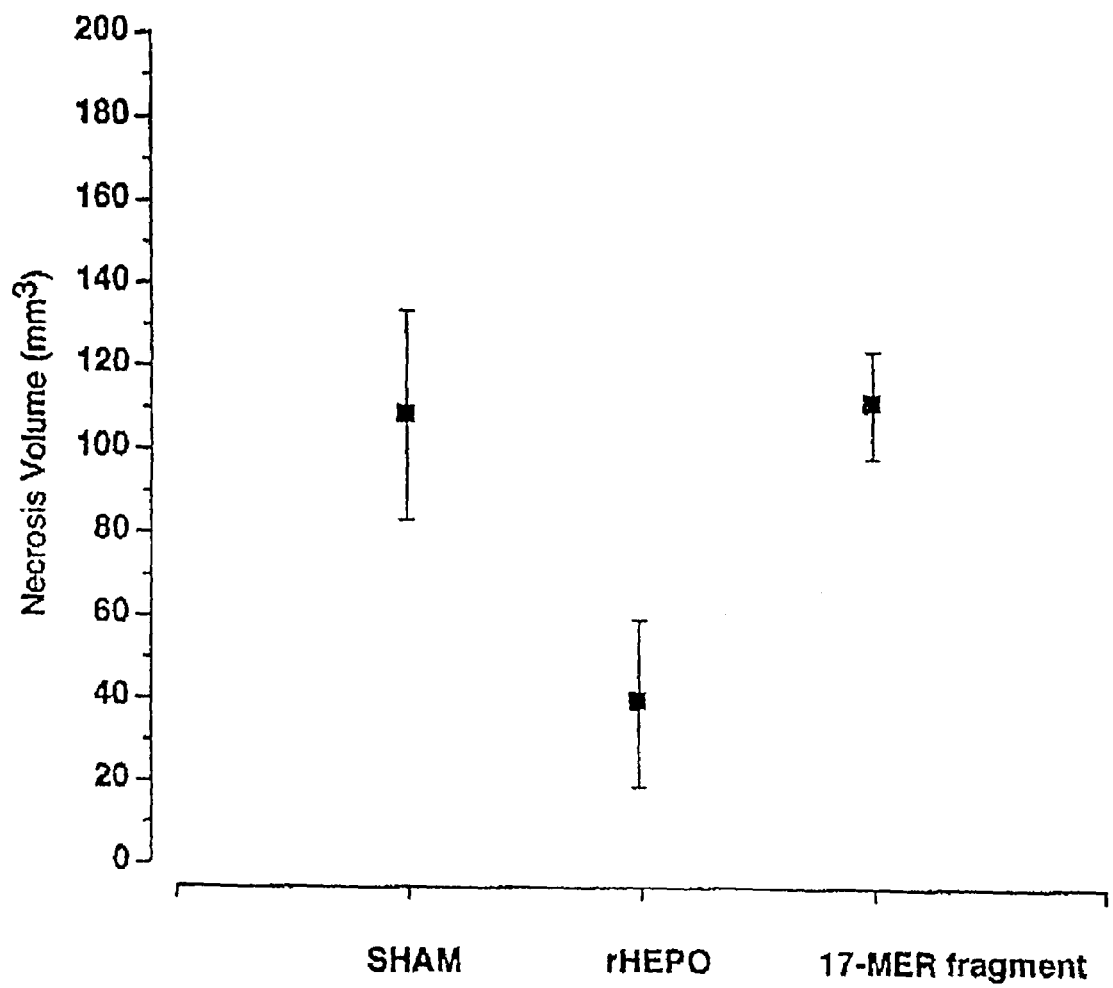

FIGS. 4A-B depicts the protective effect of rhEPO against ischemic brain injury (focal stroke). A. Systemic administration of EPO given at various times after the induction of brain ischemia reduces infarct size. B. Comparison of two forms of EPO in protecting brain from injury in this model: recombinant human (rhEPO) and 17 amino acid EPO derivative (17-mer) illustrates that some EPO analogs are ineffective for neuroprotection.

Figure 5:
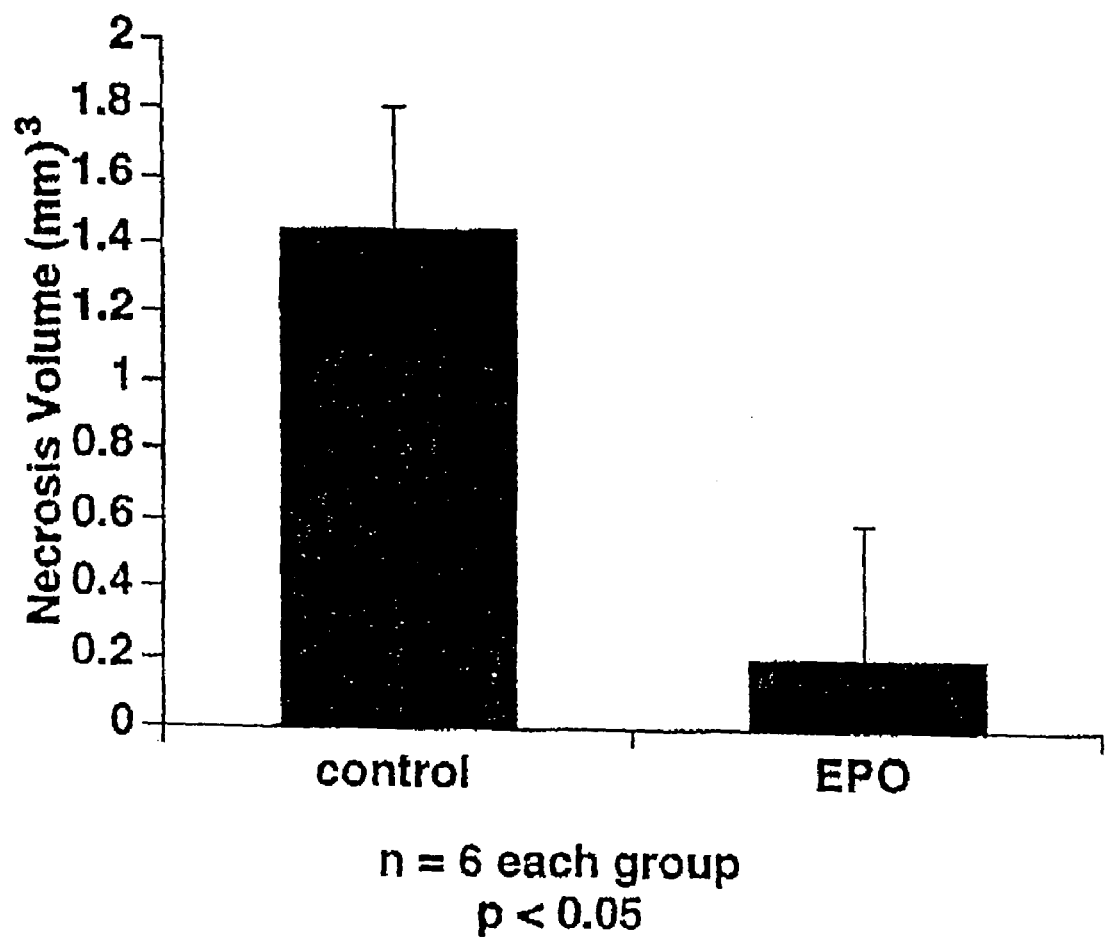

FIG. 5 depicts the protective effect of rhEPO against blunt trauma delivered to the cerebral cortex.

Figure 6A:
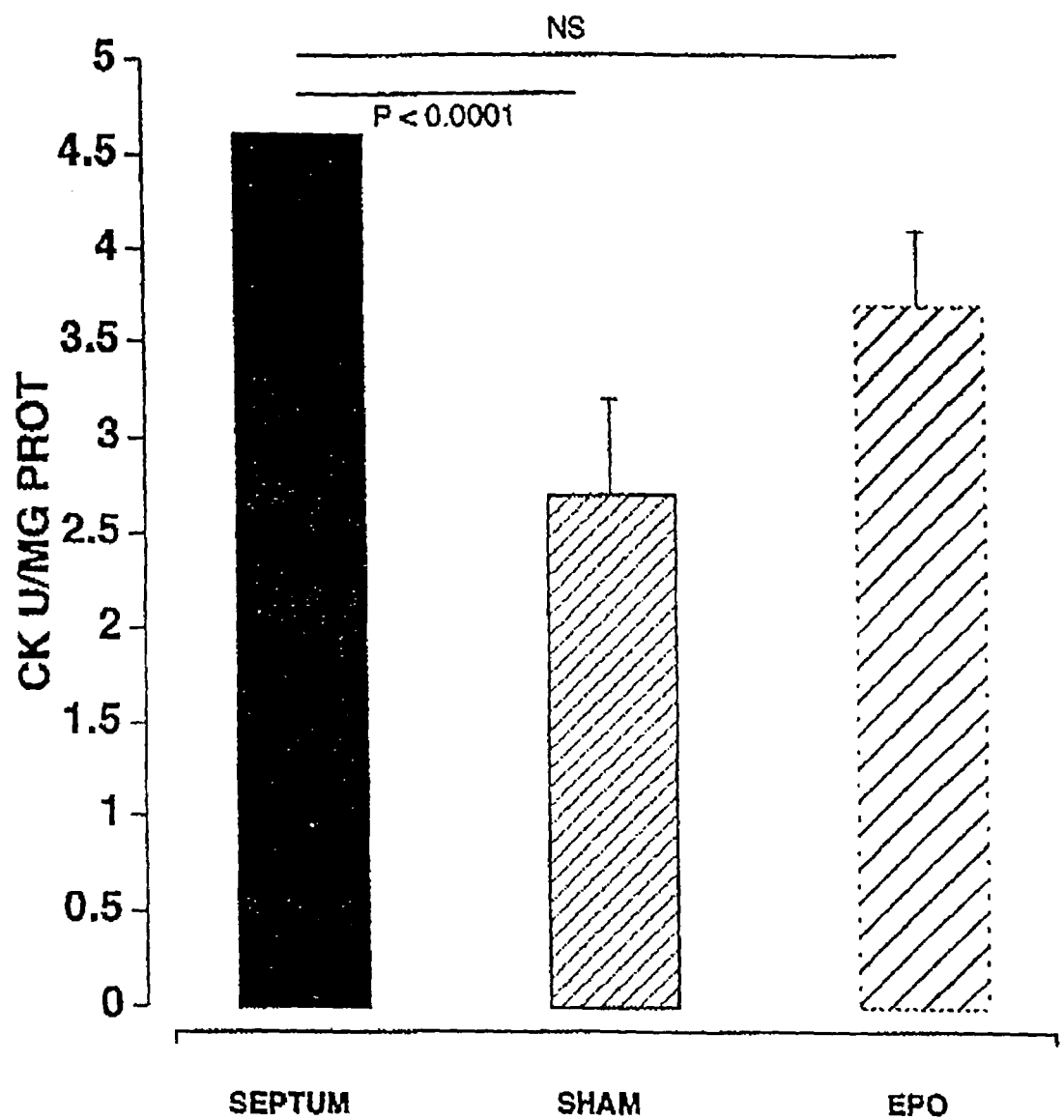
Figure 6B:
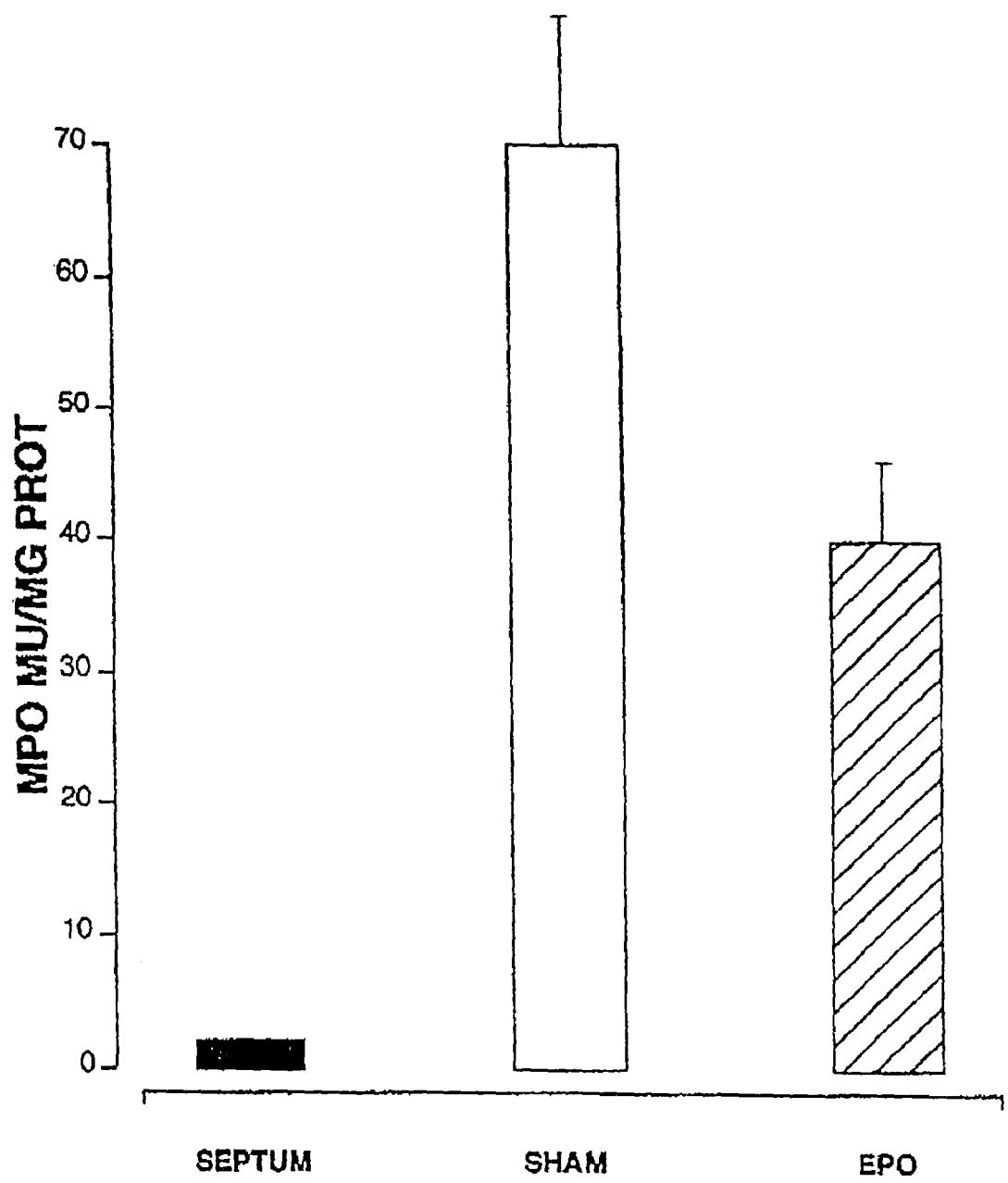

FIGS. 6A-B depicts the protective effect of EPO from ischemic heart injury. A. Creatine kinase (CK) activity, an indicator of damage to the myocardial cells. B. Myeloperoxidase (MPO) activity, a measure of inflammation.

Figure 7:
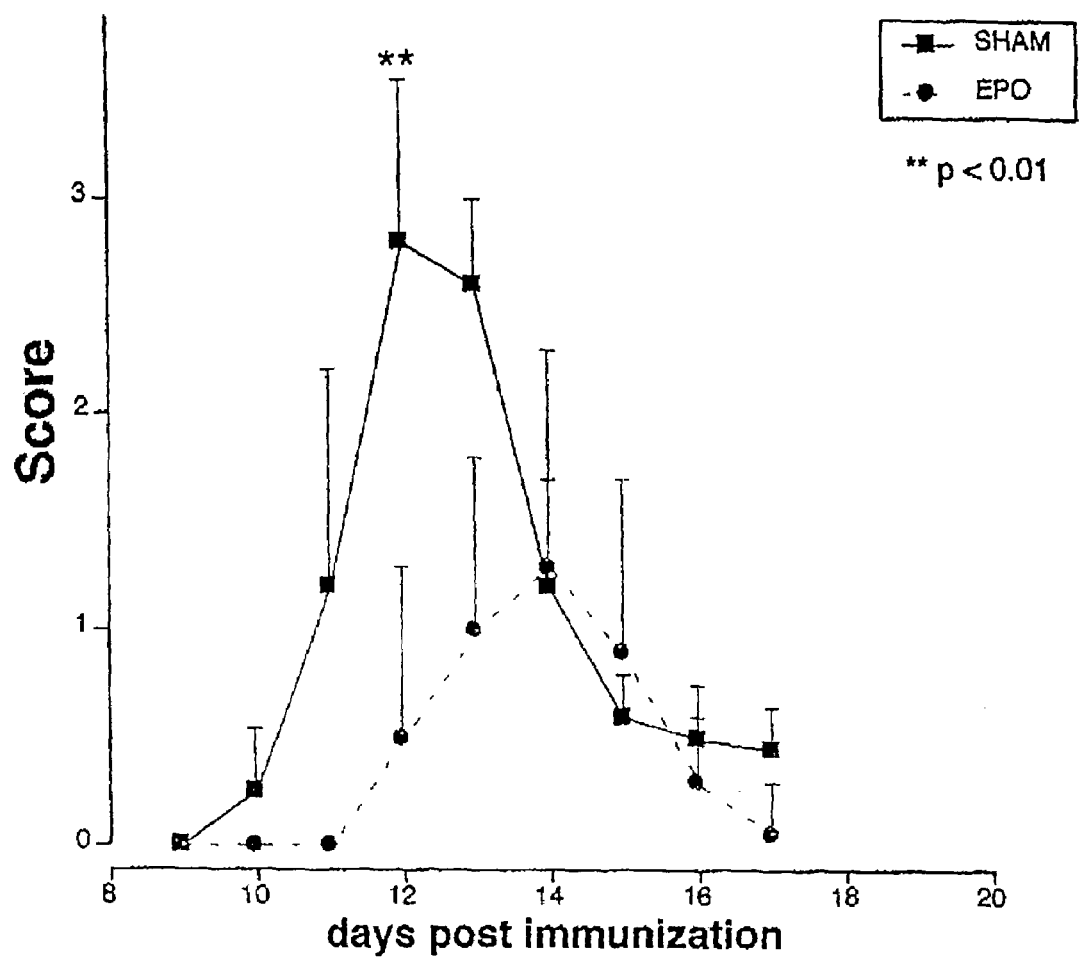

FIG. 7 shows that treatment of mice with EPO delays and reduces the neurological symptoms produced by an experimental allergic encephalitis, a model of multiple sclerosis.

Figure 8A:
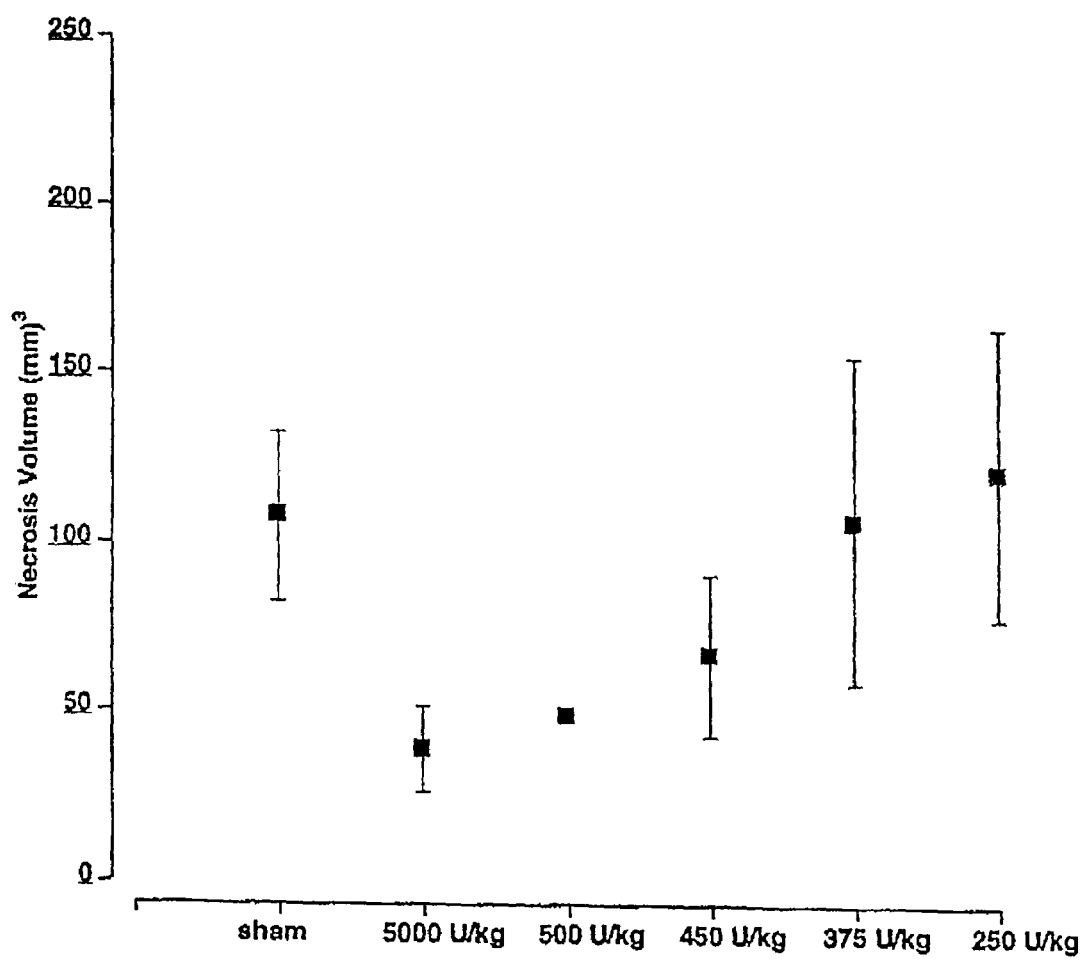
Figure 8B:
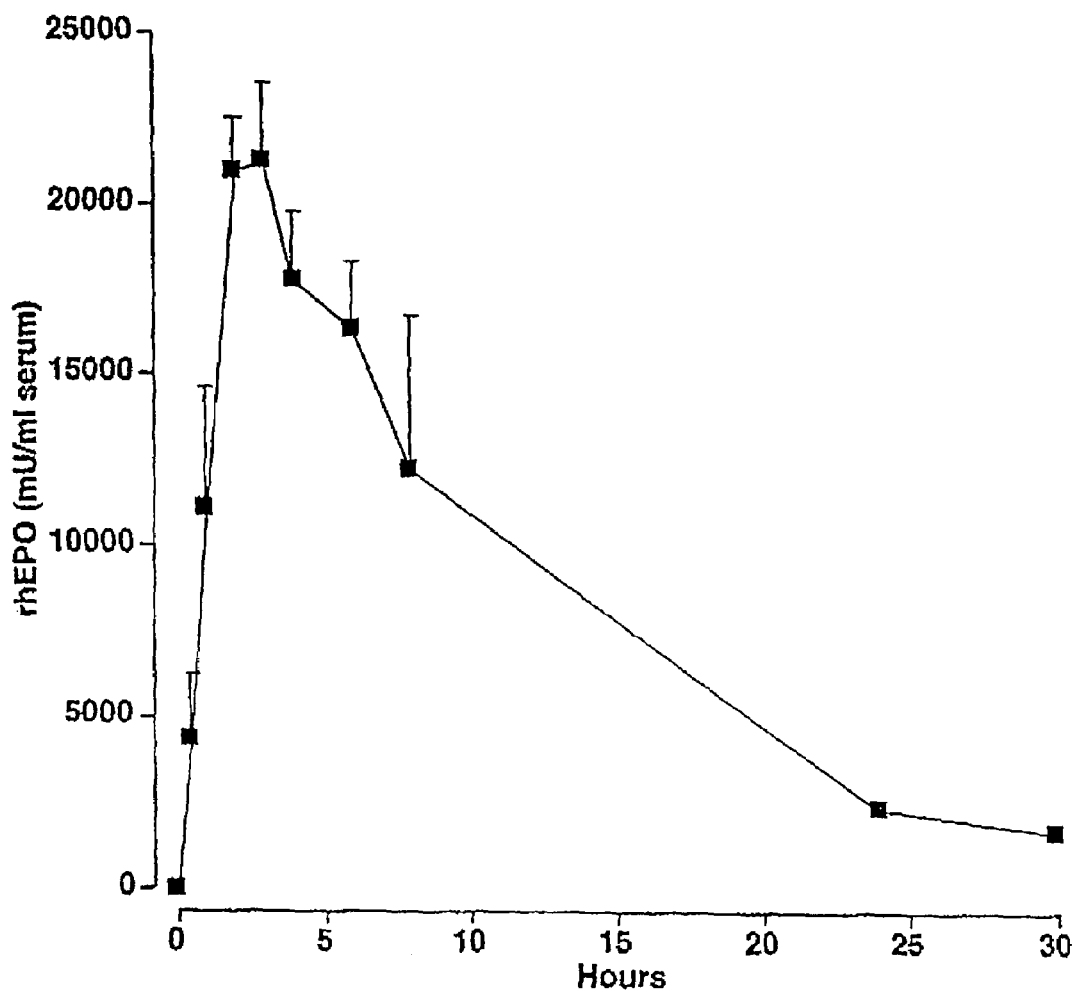

FIGS. 8A-B A. The minimum effective dose of EPO to provide neuroprotection in a focal stroke model performed in rats. B. Serum levels of EPO at various time points after 5000 U of rhEPO was administered intraperitoneally to female Balb/c mice.

Figure 9:
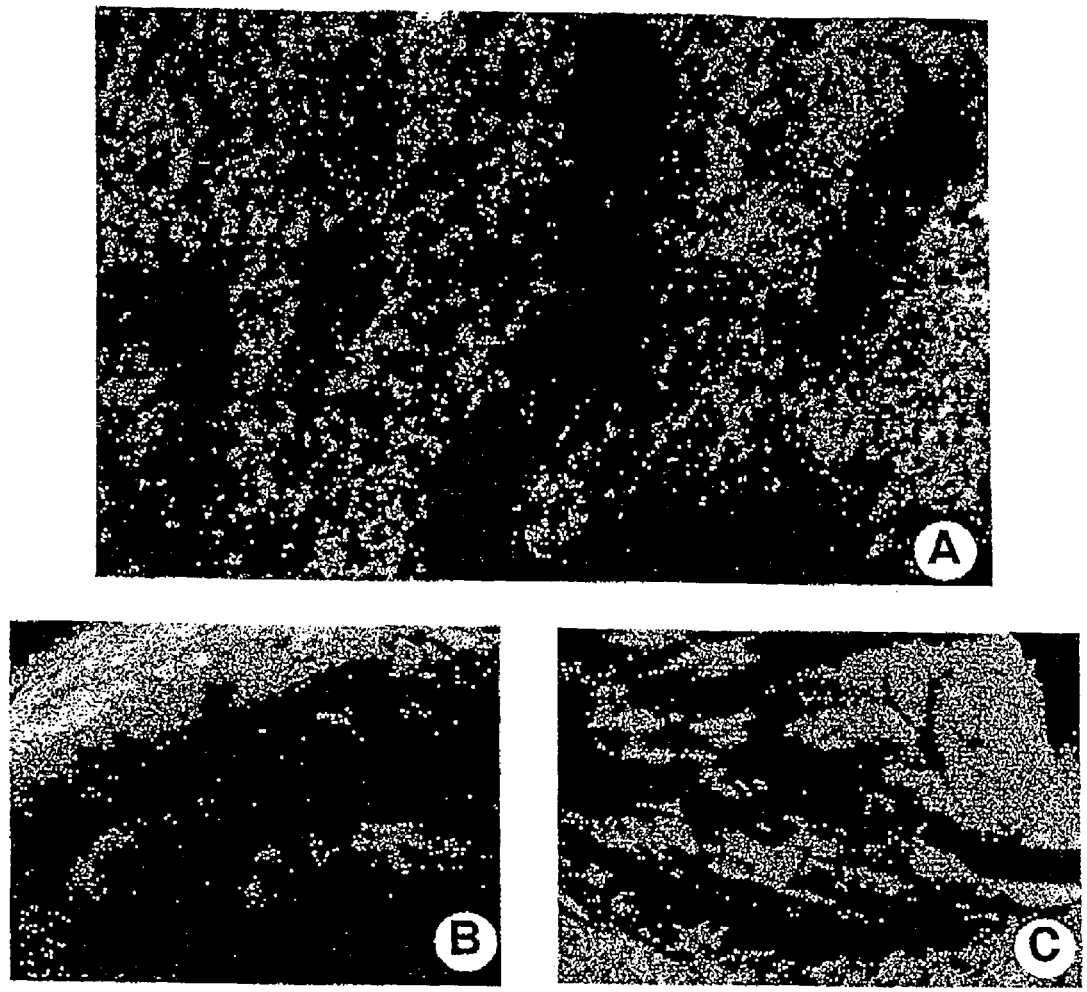

FIGS. 9A-C A. Immunolocalization of EPO-R on and around capillaries. B. Biotinylated EPO administered IP to mice is found at 5 hours within the brain immediately surrounding capillaries. C. After 17 hours, the biotin label can be found to be within specific neurons.

5. DETAILED DESCRIPTION OF THE INVENTION

The present invention provides compositions and methods for the use of erythropoietin (EPO) for modulating excitable tissue function, such as, for example, enhancing cognitive function and protecting excitable cells from toxic stimuli. In particular, the invention provides compositions comprising EPO, as well as methods for their use in prophylactic and therapeutic treatments, including drug delivery. As used herein, excitable tissue, includes, but is not limited to, neuronal tissue of the central and peripheral nervous systems, and cardiac tissue.

The invention described herein provides methods for modulating excitable tissue function by peripheral administration of EPO, or an EPO receptor activating molecule or a molecule exhibiting EPO-activated receptor activity, as well as any molecule that mimics the activity of EPO by acting through other, non-classical EPO receptors. Without being bound by any particular mechanism of action, such a molecule may signal via the EPO receptor, for example, initiates a signal transduction cascade ultimately activating a gene expression program resulting in the protection or enhancement of excitable tissue function. Molecules capable of interacting with the EPO receptor and modulating the activity of the receptor, herein referred to as EPO or EPO receptor activity modulators, are useful in the context of the present invention for the protection or enhancement of excitable tissue function. These molecules may be, for example, naturally-occurring, synthetic, or recombinant forms of EPO molecules, describe above, or other molecules which may not necessarily resemble EPO in any manner, except to modulate EPO receptor activity, as described herein. These molecules may be used in combination for the various purposes herein described.

The compositions and methods described herein can be used to treat and/or protect both normal tissue or abnormal tissue, for example, neurons of the central nervous system, neurons of the peripheral nervous system, or heart tissue. In particular, in Section 5.1, below, EPO compositions useful for practice with invention are described. In Section 5.2.1, methods are described for the use of such EPO compositions for enhancing the function of excitable tissue, such as learning, memory, and other aspects of cognitive function, and, in Section 5.2.2, methods for protecting excitable tissue from damage and injury are described. Also described in Section 5.2.3 below, the discovery of the unexpected ability of EPO to cross capillary endothelial cell tight junctions provides methods for delivery of compounds across such barriers. Finally, described in Section 5.3 are conditions that can be targeted using the methods of the invention, and in Section 5.4, methods of administration and effective dosages of such EPO compositions are described.

5.1 Compositions Comprising Erythropoietin

EPO compositions suitable for use with the invention include any erythropoietin compound that, when administered peripherally, is capable of activating EPO-activated receptors to modulate, i.e. enhance the function of, protect from damage or injury, or deliver compounds to, excitable tissue. Erythropoietin is a glycoprotein hormone which in humans has a molecular weight of 34 to 38 kD. The mature protein comprises 166 amino acids, and the glycosyl residues comprise about 40% of the weight of the molecule. The forms of EPO useful in the practice of the present invention encompass naturally-occurring, synthetic and recombinant forms of the following molecules: erythropoietin, erythropoietin analogs, erythropoietin mimetics, erythropoietin fragments, hybrid erythropoietin molecules, erythropoietin receptor-binding molecules, erythropoietin agonists, renal erythropoietin, brain erythropoietin, oligomers and multimers thereof, muteins thereof, and congeners thereof. The term "erythropoietin" and "EPO" may be used interchangeably or conjunctively.

Synthetic and recombinant molecules, such as brain EPO and renal EPO, recombinant mammalian forms of EPO, as well as its naturally-occurring, tumor-derived, and recombinant isoforms, such as recombinantly-expressed molecules and those prepared by homologous recombination are provided herein. Furthermore, the present invention includes molecules including peptides which bind the EPO receptor, as well as recombinant constructs or other molecules which possess part or all of the structural and/or biological properties of EPO, including fragments and multimers of EPO or its fragments. EPO herein embraces molecules with altered EPO receptor binding activities, preferably with increased receptor affinity, in particular as pertains to enhancing transport across endothelial cell barriers. Muteins comprising molecules which have additional or reduced numbers of glycosylation sites are included herein. As noted above, the terms "erythropoietin," "EPO," and "mimetics" as well as the other terms are used interchangeably herein to refer to the excitable tissue protective and enhancing molecules related to EPO as well as the molecules which are capable of crossing endothelial tight junctions and as such are useful as a delivery means for other molecules. Furthermore, molecules produced by transgenic animals are also encompassed here. It should be noted that EPO molecules as embraced herein do not necessarily resemble EPO structurally or in any other manner, except for ability to interact with the EPO receptor or modulate EPO receptor activity or activate EPO-activated signaling cascades, as described herein.

By way of non-limiting example, forms of EPO useful for the practice of the present invention include EPO muteins, such as those with altered amino acids at the carboxy terminus described in U.S. Pat. No. 5,457,089 and in U.S. Pat. No. 4,835,260; EPO isoforms with various numbers of sialic acid residues per molecule, such as described in U.S. Pat. No. 5,856,292; polypeptides described in U.S. Pat. No. 4,703,008; agonists described in U.S. Pat. No. 5,767,078; peptides which bind to the EPO receptor as described in U.S. Pat. Nos. 5,773,569 and 5,830,851; small-molecule mimetics which activate the EPO receptor, as described in U.S. Pat. No. 5,835,382; and EPO analogs described in WO 9505465, WO 9718318, and WO 9818926. All of the aforementioned citations are incorporated herein to the extent that such disclosures refer to the various alternate forms or processes for preparing such forms of the erythropoietins of the present invention.

EPO can be obtained commercially (under the trademarks of PROCRIT, available from Ortho Biotech, and EPOGEN, available from Amgen, Inc., Thousand Oaks, Calif.).

In a further embodiment of the present invention, the EPO molecules embraced herein include hybrid EPO molecules that may be prepared which comprise the EPO receptor modulating activity as well as another activity, for example, that of growth hormone. Such hybrid molecules with multiple domains thus possess the ability to interact with the EPO receptor—as well as having the activity of another molecule such as a hormone. Methods of preparation of such molecules with two domains are known to one skilled in the art. As will be described in more detail in Section 5.2.3 below, one feature of such molecules is transport across endothelial cell barriers provided by the EPO receptor activity modulating domain, and activity of the other molecule at the target site.

Any of the compounds described above may be tested to identify EPO compounds capable of modulating excitable tissue, i.e. enhance the function of, protect from damage or injury, or deliver compounds thereto, using the assays described herein. For example, EPO compounds may be tested for their ability to enhance the function of excitable tissue, such as learning, memory, and other aspects of cognitive function using the methods described in Section 5.2.1. Examples of in vivo assays for cognitive function include the Morris Water Maze test, an example of which is described in Section 6, and the Conditioned Taste Aversion test, an example of which is described in detail in Section 7. In addition, the EPO compounds described above may be tested using assays described in Section 5.2.2, to identify EPO compounds capable of protecting excitable tissue from damage and injury. The Examples described in Sections 8, 9, 10, 11, and 12 provide specific examples of such assays. EPO compounds may also be assayed for their capacity to delivery of compounds across epithelial tight junctions, such as the blood-brain barrier, using assays such as those described in Section 5.2.3 and Section 9, below. Thus, EPO compositions suitable for use with the invention include any and all compounds that, when administered peripherally, are capable of signaling through EPO-activated receptors to modulate excitable tissue, i.e. enhance the function of, protect from damage or injury, or deliver compounds thereto.

5.2 Methods for Prophylactic and Therapeutic Use of the Invention

In various embodiments of the invention, EPO compositions can be used for protecting excitable tissue from injury or hypoxic stress, enhancing the function of excitable tissue, or for delivery of compounds across endothelial tight junctions of excitable tissue. As described above, the invention is based, in part, on the discovery that EPO molecules can be transported from the luminal surface to the basement membrane surface of endothelial cells of the capillaries of organs with endothelial cell tight junctions, including, for example, the brain, retina, and testis. While not wishing to be bound by any particular theory, after transcytosis of EPO, EPO can interact with an EPO receptor on excitable tissue, such as, for example, neurons of the central nervous system, the peripheral nervous system, or heart tissue, and receptor binding can initiate a signal transduction cascade resulting in the activation of a gene expression program within the excitable tissue, resulting in the protection of the cell from damage, such as by neurotoxins, hypoxia, etc. Thus, methods for protecting excitable tissue from injury or hypoxic stress, enhancing the function of excitable tissue, and delivering compounds across tight junctions of excitable tissue are described in detail hereinbelow.

5.2.1 Methods for Enhancing Excitable Tissue Function

In one aspect, the present invention is directed to a method for enhancing the function of excitable tissue by administration of an EPO molecule capable of activating a gene expression program that enhances excitable tissue function. Enhancement of excitable tissue function provides enhancement of learning, associative learning, and memory. Various diseases and conditions are amenable to treatment using this method, and further, this method is useful for enhancing cognitive function in the absence of any condition or disease. These uses of the present invention are described in further detail below, and include enhancement of learning and training in both human and non-human mammals.

Conditions and diseases treatable by the methods of this aspect of the present invention include any condition or disease that can benefit from enhancement of neuronal function. Examples of such disorders include disorders of the central nervous system including, but not limited, to mood disorders, anxiety disorders, depression, autism, attention deficit hyperactivity disorder, and cognitive dysfunction. Other non-limiting examples of cognitive functions which can be enhanced using the methods of the invention are described in Section 5.3.

In one embodiment, for example, an EPO molecule may be administered to a subject or patient who is suffering from a disorder resulting in loss of cognitive functions, such, for example, as Alzheimer's Disease.

The ability of EPO to enhance cognitive functions can be tested in experimental animals using any of the methods described herein, or any other art-accepted learning or cognitive function model. As described in the Examples presented in Sections 6 and 7, peripherally-administered erythropoietin was discovered to enhance learning and cognitive function as demonstrated by several well established learning models in normal experimental animals. Examples of such learning models are the Morris water maze test, an example of which is given in Section 6 and the conditioned taste aversion (CTA) test, an example of which is given in Section 7. In one embodiment, for example, the conditioned taste aversion (CTA), a very sensitive, well known, standard test is used to test an animal's cognitive function after administration of EPO. CTA is used to test an animal's ability for learning to associate illness with a novel stimuli, such as taste, such that the animals avoid the novel taste upon subsequent re-exposure to the novel stimuli. CTA involves the brain at a variety of cortical and subcortical levels. The association which links ascending and descending information together producing aversive behavior can be either attenuated or strengthened by changes affecting any of the interconnecting units. As a form of associative learning, the strength of CTA is determined by a large number of variables including novelty of the oral stimulus (e.g., non-novel stimuli cannot be aversively conditioned), degree of "illness" produced (toxicity), number of repetitions (training), countering drives (such as thirst) to name a few. Although a wide variety of chemical and physical agents can produce CTA in a dose-dependent manner, lithium chloride reliably produces malaise and anorexia. Like a naturally occurring illness, lithium produces a CTA by stimulating the pathways described above, including cytokine release.

Enhancement of excitable cell function, for example, cognitive function, offers numerous benefits to individuals in the educational and work environment, and to enhance the ability to train and educate non-human mammals.

5.2.2 Methods for Protecting Excitable Tissue from Injury

In another embodiment, the present invention is directed toward a method for protecting a mammal from pathology resulting from injury to excitable tissue. Protection is provided by administering to a mammal by a peripheral route of administration an amount of erythropoietin effective to protect the excitable tissue from injury. As is shown in detail in the example in Section 8, below, EPO administered in advance of the toxin kainate is markedly neuroprotective in mice, raising seizure threshold and preventing death. The neuroprotective effect EPO is large and is sustained. It is notable that the positive effects seen herein occur within too short of a time relative to the administration of an EPO to be a result of an increase in hematocrit as a consequence of the erythropoietic activity of EPO. Furthermore, as noted above, an embodiment of the present invention comprises an EPO which lacks the ability to increase hematocrit.

In one embodiment, the present invention may be used advantageously both in the acute and chronic prophylaxis and treatment of neurological disorders, as described herein, and in enhanced cognitive function of the normal or the diseased brain. As noted above, damage and death of neurons in the central nervous system is a serious and often lethal occurrence responsible for a high degree of morbidity and mortality in the population. Acute neurological damage may occur during or as a result of seizures, convulsions, epilepsy, stroke, hemorrhage, central nervous system injury, hypoxia, hypoglycemia, hypotension and brain or spinal cord trauma. The present invention provides for acute administration for the treatment of acute events.

In one embodiment, for example, the methods of the invention may be used to protect a mammal from injury resulting from radiation damage to the brain.

In another embodiment, a serious condition treatable or preventable in accordance with the present invention is prophylaxis and treatment in utero of prenatal hypoxic conditions, post-birth treatment to protect the brain from hypoxic injury sustained during birth, as well as in suffocation, drowning, and other conditions wherein the central nervous system is at risk for neurotoxic damage as a result of oxygen deprivation or exposure to other neurotoxic stimuli. As is well known, individuals who suffer from hypoxia during labor, or as a consequence of non-fatal hypoxic accidents or incidents may suffer a lifelong neurologic deficit. Hypoxia and/or cessation of cerebral blood flow, which may occur post-trauma or during surgical procedures, also carries a risk of causing lifelong neurologic deficit.

Postoperative cognitive dysfunction, including deficits following the use of a heart-lung machine, are also treatable by the methods provided herein. Furthermore, the present methods may be applied to the treatment of hypoxia resulting from carbon monoxide poisoning or smoke inhalation.

In another embodiment, EPO is used to protect cardiac tissue from injury sustained during ischemia, infarction, inflammation, or trauma.

These are non-limiting examples of damage to excitable tissue treatable in accordance with the present invention. Acute and early treatment of these disorders may be carried out by mobile medical emergency health care professionals such that treatment may be started as soon as suspicion of potential for neurologic damage is ascertained. Risk of neurologic damage induced by labor may be reduced by prophylactically treatment of the fetus before or during labor. These and other utilities and situations will be recognized by the skilled artisan.

5.2.3 Methods for Delivery of Compounds

The present invention is further directed to a method for facilitating the transport of a molecule across an endothelial cell barrier in a mammal by administering a composition which comprises the particular molecule in association with erythropoietin. As noted above, the inventors herein discovered the heretofore unexpected and surprising activity of peripherally-administered EPO on excitable tissue, such as nervous tissue in the central nervous system, the peripheral nervous system, or heart tissue, identifying EPO as a molecule capable of crossing tight junctions of such excitable tissue, such as the blood-brain barrier. As such, EPO is useful as a carrier for delivering other molecules across the blood-brain and other similar barriers.

In one embodiment, EPO receptor binding molecules comprising molecules conjugated to an EPO molecule, may be used to transport those molecules across the blood brain barrier. Such molecules can thereby piggyback on EPO for delivery across the BBB. In another embodiment, an antibody or other binding partner to the molecule may be associated with EPO, or with an EPO receptor activity modulator, thus associating the molecule to be transported by noncovalent binding to the binding partner, which is further associated with the transportable EPO molecule. In another embodiment, EPO receptor-binding molecules comprising antibodies to the EPO receptor are useful for the method described here. Such antibodies provide a transport carrier on which other molecules may hitchhike, much in the same fashion that antibodies to the transferrin receptor have been used to gain access across the blood-brain (Pardridge et al., 1991, Selective transport of an antitransferrin receptor antibody through the blood-brain barrier in vivo. J. Pharmacol. Exp. Therap. 27: 66).

The skilled artisan will be aware of various means for associating molecules with EPO and the other agents described above, by covalent, non-covalent, and other means; furthermore, evaluation of the efficacy of the composition may be readily determined in an experimental system. Association of molecules with EPO and analogs may be achieved by any number of means, including labile, covalent binding, cross-linking, etc. In one embodiment, for example, the association between the molecule to be transported across the barrier and the erythropoietin may be a labile covalent bond, in which case the molecule is released from association with the EPO after crossing the barrier. In one embodiment, biotin/avidin interactions may be employed. In another embodiment, as mentioned above, a hybrid molecule may be prepared by recombinant or synthetic means, for example, which includes both the domain of the molecule with desired pharmacological activity and the domain responsible for EPO receptor activity modulation.

A molecule may be conjugated to an EPO or EPO receptor activity modulator through a polyfunctional molecule, i.e., a polyfunctional crosslinker. As used herein, the term "polyfunctional molecule" encompasses molecules having one functional group that can react more than one time in succession, such as formaldehyde, as well as molecules with more than one reactive group. As used herein, the term "reactive group" refers to a functional group on the crosslinker that reacts with a functional group on a molecule (e.g., peptide, protein, carbohydrate, nucleic acid, particularly a hormone, antibiotic, or anti-cancer agent to be delivered across an endothelial cell barrier) so as to form a covalent bond between the cross-linker and that molecule. The term "functional group" retains its standard meaning in organic chemistry. The polyfunctional molecules which can be used are preferably biocompatible linkers, i.e., they are noncarcinogenic, nontoxic, and substantially non-immunogenic in vivo. Polyfunctional cross-linkers such as those known in the art and described herein can be readily tested in animal models to determine their biocompatibility. The polyfunctional molecule is preferably bifunctional. As used herein, the term "bifunctional molecule" refers to a molecule with two reactive groups. The bifunctional molecule may be heterobifunctional or homobifunctional. A heterobifunctional cross-linker allows for vectorial conjugation. It is particularly preferred for the polyfunctional molecule to be sufficiently soluble in water for the cross-linking reactions to occur in aqueous solutions such as in aqueous solutions buffered at pH 6 to 8, and for the resulting conjugate to remain water soluble for more effective bio-distribution. Typically, the polyfunctional molecule covalently bonds with an amino or a sulfhydryl functional group. However, polyfunctional molecules reactive with other functional groups, such as carboxylic acids or hydroxyl groups, are contemplated in the present invention.

The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde. The use of glutaraldehyde as a cross-linking agent was disclosed by Poznansky et al., Science 223, 1304-1306 (1984). Homobifunctional molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts. These homobifunctional reagents are available from Pierce, Rockford, Ill.

The heterobifunctional molecules have at least two different reactive groups. The reactive groups react with different functional groups, e.g., present on the EPO and the molecule. These two different functional groups that react with the reactive group on the heterobifunctional cross-linker are usually an amino group, eg., the epsilon amino group of lysine; a sulfhydryl group, e.g., the thiol group of cysteine; a carboxylic acid, e.g., the carboxylate on aspartic acid; or a hydroxyl group, e.g., the hydroxyl group on serine.

When a reactive group of a heterobifunctional molecule forms a covalent bond with an amino group, the covalent bond will usually be an amido or imido bond. The reactive group that forms a covalent bond with an amino group may, for example, be an activated carboxylate group, a halocarbonyl group, or an ester group. The preferred halocarbonyl group is a chlorocarbonyl group. The ester groups are preferably reactive ester groups such as, for example, an N-hydroxy-succinimide ester group.

The other functional group typically is either a thiol group, a group capable of being converted into a thiol group, or a group that forms a covalent bond with a thiol group. The covalent bond will usually be a thioether bond or a disulfide. The reactive group that forms a covalent bond with a thiol group may, for example, be a double bond that reacts with thiol groups or an activated disulfide. A reactive group containing a double bond capable of reacting with a thiol group is the maleimido group, although others, such as acrylonitrile, are also possible. A reactive disulfide group may, for example, be a 2-pyridyldithio group or a 5,5'-dithiobis-(2-nitrobenzoic acid) group. Some examples of heterobifunctional reagents containing reactive disulfide bonds include N-succinimidyl 3-(2-pyridyl-dithio)propionate (Carlsson et al., 1978, Biochem J., 173:723-737), sodium 5-4-succinimidyloxycarbonyl-alpha-methylbenzylthiosulfate, and 4-succinimidyloxycarbonyl-alpha-methyb(2-pyridyldithio)toluene. N-succinimidyl 3-(2-pyridyldithio)propionate is preferred. Some examples of heterobifunctional reagents comprising reactive groups having a double bond that reacts with a thiol group include succinimidyl 4-(N-maleimidomethyl)cyclohexane-1-carboxylate and succinimidyl m-maleimidobenzoate.

Other heterobifunctional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-N-hydroxy-succinimide ester. The sodium sulfonate salt of succinimidyl m-maleimidobenzoate is preferred. Many of the above-mentioned heterobifunctional reagents and their sulfonate salts are available from Pierce.

The need for the above-described conjugated to be reversible or labile may be readily determined by the skilled artisan. A conjugate may be tested in vitro for both the EPO receptor activity modulation activity, and for the desirable pharmacological activity. If the conjugate retains both properties, its suitability may then be tested in vivo. If the conjugated molecule requires separation from the EPO for activity, a labile bond or reversible association with EPO will be preferable. The liability characteristics may also be tested using standard in vitro procedures before in vivo testing.

Additional information regarding how to make and use these as well as other polyfunctional reagents may be obtained from the following publications or others available in the art: Carlsson et al., 1978, Biochem. J. 173:723-737; Cumber et al., 1985, Methods in Enzymology 112:207-224; Jue et al., 1978, Biochem. 17:5399-5405; Sun et al., 1974, Biochem. 13:2334-2340; Blattler et al., 1985, Biochem. 24:1517-152; Liu et al., 1979, Biochem. 18:690-697; Youle and Neville, 1980, Proc. Natl. Acad. Sci. U.S.A. 77:5483-5486; Lerner et al., 1981, Proc. Natl. Acad. Sci. U.S.A. 78:3403-3407; Jung and Moroi, 1983, Biochem. Biophys. Acta 761:162; Caulfield et al., 1984, Biochem. 81:7772-7776; Staros, J. V., 1982, Biochem. 21:3950-3955; Yoshitake et al., 1979, Eur. J. Biochem. 101:395-399; Yoshitake et al., 1982, J. Biochem. 92:1413-1424; Pilch and Czech, 1979, J. Biol. Chem. 254:3375-3381; Novick et al., 1987, J. Biol. Chem. 262:8483-8487; Lomant and Fairbanks, 1976, J. Mol. Biol. 104:243-261; Hamada and Tsuruo, 1987, Anal. Biochem. 160:483-488; and Hashida, 1984, J. Applied Biochem. 6:56-63. Additionally, methods of cross-linking are reviewed by Means and Feeney, 1990, Bioconjugate Chem. 1:2-12. Barriers which are crossed by the above-described methods and compositions of the present invention include but are not limited to the blood-brain barrier, the blood-eye barrier, the blood-testes barrier, the blood-ovary barrier, and the blood-placenta barrier.

Candidate molecules for transport across an endothelial cell barrier include, for example, hormones such as growth hormone, neurotrophic factors, antibiotics or antifungals such as those normally excluded from the brain and other barriered organs, peptide radiopharmaceuticals, antisense drugs, antibodies against biologically-active agents, pharmaceuticals, and anti-cancer agents. Non-limiting examples of such molecules include growth hormone, nerve growth factor (NGF), brain-derived neurotrophic factor (BNF), ciliary neurotrophic factor (CTF.), basic fibroblast growth factor (bFGF), transforming growth factor β1 (TGFβ1), transforming growth factor β2 (TGFβ2), transforming growth factor β3 (TGFβ3), interleukin 1, interleukin 2, interleukin 3, and interleukin 6, AZT, antibodies against tumor necrosis factor, and immunosuppressive agents such as cyclosporin.

In another embodiment, recombinant chimeric toxin molecules comprising EPO can be used for therapeutic delivery of toxins to treat a viral disorder or proliferative disorder, such as cancer. Compounds that could be fused to EPO to construct a chimeric toxin suitable for this embodiment include, but are not limited to, toxic substances, such as pseudomonas exotoxin, diphtheria toxin, and ricin, among others.

5.3 Target Conditions

As described above, the EPO compositions and methods for their use provided herein can be used to treat and prevent conditions arising from hypoxic conditions, which adversely affect excitable tissues, such as excitable tissues in the central nervous system tissue, peripheral nervous system tissue, or cardiac tissue such as, for example, brain, heart, or retina. Therefore, the invention can be used to treat or prevent damage to excitable tissue resulting from hypoxic conditions in a variety of conditions and circumstances. Non-limiting examples of such conditions and circumstances are provided hereinbelow.

In the example of the protection of neuronal tissue pathologies treatable in accordance with the present invention, such pathologies include those which result from reduced oxygenation of neuronal tissues. Any condition which reduces the availability of oxygen to neuronal tissue, resulting in stress, damage, and finally, neuronal cell death, can be treated by the methods of the present invention. Generally referred to as hypoxia and/or ischemia, these conditions arise from or include, but are not limited to stroke, vascular occlusion, prenatal or postnatal oxygen deprivation, suffocation, choking, near drowning, carbon monoxide poisoning, smoke inhalation, trauma, including surgery and radiotherapy, asphyxia, epilepsy, hypoglycemia, chronic obstructive pulmonary disease, emphysema, adult respiratory distress syndrome, hypotensive shock, septic shock, anaphylactic shock, insulin shock, sickle cell crisis, cardiac arrest, dysrhythmia, and nitrogen narcosis.

In one embodiment, for example, EPO may be administered to prevent injury or tissue damage resulting from risk of injury or tissue damage during surgical procedures, such as, for example, tumor resection or aneurysm repair.

Other pathologies caused by or resulting from hypoglycemia which are treatable by the methods described herein include insulin overdose, also referred to as iatrogenic hyperinsulinemia, insulinoma, growth hormone deficiency, hypocortisolism, drug overdose, and certain tumors.

Other pathologies resulting from excitable neuronal tissue damage include seizure disorders, such as epilepsy, convulsions, or chronic seizure disorders. Other treatable conditions and diseases include diseases such as stroke, multiple sclerosis, hypotension, cardiac arrest, Alzheimer's disease, Parkinson's disease, cerebral palsy, brain or spinal cord trauma, AIDS dementia, age-related loss of cognitive function, memory loss, amyotrophic lateral sclerosis, seizure disorders, alcoholism, retinal ischemia, optic nerve damage resulting from glaucoma, and neuronal loss.

The methods of the invention may be used to treat conditions of, and damage to, retinal tissue. Such disorders include, but are not limited to macular degeneration, retinal detachment, retinitis pigmentosa, arteriosclerotic retinopathy, hypertensive retinopathy, retinal artery blockage, retinal vein blockage, hypotension, and diabetic retinopathy.

In another embodiment, the methods of the invention may be used to protect or treat injury resulting from radiation damage to excitable tissue.

A further utility of the methods of the present invention is in the treatment of neurotoxin poisoning, such as demonic acid shellfish poisoning, neurolathyrism, and Guam disease, amyotrophic lateral sclerosis, and Parkinson's disease.

As mentioned above, the present invention is also directed to a method for enhancing excitable tissue function in a mammal by peripheral administration of erythropoietin. Various diseases and conditions are amenable to treatment using this method, and further, this method is useful for enhancing cognitive function in the absence of any condition or disease. These uses of the present invention are described in further detail below, and include enhancement of learning and training in both human and non-human mammals.

Conditions and diseases treatable by the methods of this aspect of the present invention directed to the central nervous system include but are not limited to mood disorders, anxiety disorders, depression, autism, attention deficit hyperactivity disorder, and cognitive dysfunction. These conditions benefit from enhancement of neuronal function.

Other disorders treatable in accordance with the teachings of the present invention include sleep disruption, for example, sleep apnea and travel-related disorders; subarachnoid and aneurysmal bleeds, hypotensive shock, concussive injury, septic shock, anaphylactic shock, and sequelae of various encephalitides and meningitides, for example, connective tissue disease-related cerebritides such as lupus. Other uses include prevention of or protection from poisoning by neurotoxins, such as domoic acid shellfish poisoning, neurolathyrism, and Guam disease, amyotrophic lateral sclerosis, Parkinson's disease; postoperative treatment for embolic or ischemic injury; whole brain irradiation; sickle cell crisis; and eclampsia.

A further group of conditions treatable by the methods of the present invention include mitochondrial dysfunction, of either an hereditary or acquired nature, which are the cause of a variety of neurological diseases typified by neuronal injury and death. For example, Leigh disease (subacute necrotizing encephalopathy) is characterized by progressive visual loss and encephalopathy, due to neuronal drop out, and myopathy. In these cases, defective mitochondrial metabolism fails to supply enough high energy substrates to fuel the metabolism of excitable cells. An EPO receptor activity modulator optimizes failing function in a variety of mitochondrial diseases.

As mentioned above, hypoxic conditions adversely affect excitable tissues. The excitable tissues include, but are not limited to, central nervous system tissue, peripheral nervous system tissue, and heart tissue. In addition to the conditions described above, the methods of the present invention are useful in the treatment of inhalation poisoning such as carbon monoxide and smoke inhalation, severe asthma, adult respiratory distress syndrome, and choking and near drowning. Further conditions which create hypoxic conditions or by other means induce excitable tissue damage include hypoglycemia that may occur in inappropriate dosing of insulin, or with insulin-producing neoplasms (insulinoma).

Various neuropsychologic disorders which are believed to originate from excitable tissue damage are treatable by the instant methods. Chronic disorders in which neuronal damage may be involved and for which treatment by the present invention is provided include disorders relating to the central nervous system and/or peripheral nervous system including age-related loss of cognitive function and senile dementia, chronic seizure disorders, Alzheimer's disease, Parkinson's disease, dementia, memory loss, amyotrophic lateral sclerosis, multiple sclerosis, tuberous sclerosis, Wilson's Disease, cerebral and progressive supranuclear palsy, Guam disease, Lewy body dementia, prion diseases, such as spongiform encephalopathies, e.g., Creutzfeldt-Jakob disease, Huntington's disease, myotonic dystrophy, Freidrich's ataxia and other ataxias, as well as Gilles de la Tourette's syndrome, seizure disorders such as epilepsy and chronic seizure disorder, stroke, brain or spinal cord trauma, AIDS dementia, alcoholism, autism, retinal ischemia, glaucoma, autonomic function disorders such as hypertension and sleep disorders, and neuropsychiatric disorders that include, but are not limited to schizophrenia, schizoaffective disorder, attention deficit disorder, dysthymic disorder, major depressive disorder, mania, obsessive-compulsive disorder, psychoactive substance use disorders, anxiety, panic disorder, as well as unipolar and bipolar affective disorders. Additional neuropsychiatric and neurodegenerative disorders include, for example, those listed in the American Psychiatric Association's Diagnostic and Statistical manual of Mental Disorders (DSM), the most current version of which is incorporated herein by reference in its entirety.

In another embodiment, recombinant chimeric toxin molecules comprising EPO can be used for therapeutic delivery of toxins to treat a proliferative disorder, such as cancer, or viral disorder, such as subacute sclerosing panencephalitis.

5.4 Pharmaceutical Preparations and Administration

According to the invention, EPO, its analogues, mimetics, erythropoietin fragments, hybrid erythropoietin molecules, erythropoietin receptor-binding molecules, erythropoietin agonists, renal erythropoietin, brain erythropoietin, muteins thereof, and congeners thereof, may be introduced parenterally, transmucosally, e.g., orally, nasally, rectally, intravaginally, sublingually, submucosally or transdermally. Preferably, administration is parenteral, e.g., via intravenous or intraperitoneal injection, and also including, but is not limited to, intra-arterial, intramuscular, intradermal and subcutaneous administration. The preferred route of administration of small molecule EPO mimetics is by the oral route.

A subject in whom peripheral administration of EPO is an effective therapeutic regiment is preferably a human, but can be any animal, preferably a mammal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc. As noted above, domesticated animals, including pets and work animals, are candidates for both the neuroprotective benefits of the present invention, as well as the enhancement of cognitive function. Neurological damage arising from hypoxia, and well as acute and chronic disorders including epilepsy, are common among such animals, and thus are candidates for treatment. Also as noted above, cognitive enhancement in non-human animals is a benefit of the present invention, in that learning, training, and retention of learned behavior may be enhanced, reinforced, and maintained using the teachings of the present invention. As such, the expense and psychological strain to the pet owner is reduced. For example, the time required for training dogs and other domestic animals is reduced. Furthermore, wild animals typically difficult to train may be better candidates for training by the methods of the present invention.

5.4.1 Formulation and Effective Dose

The present invention also provides pharmaceutical compositions. Pharmaceutical compositions comprising EPO and EPO receptor activity modulators can be administered to a patient at therapeutically effective doses to protect excitable tissue from damage, enhance the function of excitable tissue, or to deliver a compound to excitable tissue. The Applicants have discovered that an elevated dose of EPO is preferred to modulate excitable tissue, and to protect against injury thereto.

Selection of the preferred effective dose will be determined by a skilled artisan based upon considering several factors which will be known to one of ordinary skill in the art. Such factors include the particular form of erythropoietin, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, according to standard clinical techniques.

In one embodiment, the invention provides a pharmaceutical composition in dosage unit form adapted for modulation of excitable tissue, enhancement of cognitive function or delivery of compounds across endothelial tight junctions which comprises, per dosage unit, an effective non-toxic amount within the range from about 50,000 to 500,000 Units, 60,000 to 500,000 Units, 70,000 to 500,000 Units, 80,000 to 500,000 Units, 90,000 to 500,000 Units, 100,000 to 500,000 Units, 150,000 to 500,000 Units, 200,000 to 500,000 Units, 250,000 to 500,000 Units, 300,000 to 500,000 Units, 350,000 to 500,000 Units, 400,000 to 500,000 Units, or 450,000 to 500,000 Units of EPO, an EPO receptor activity modulator, or an EPO-activated receptor modulator and a pharmaceutically acceptable carrier. In a preferred embodiment, the effective non-toxic amount of EPO is within the range from about 50,000 to 500,000 Units.

In one embodiment, such a pharmaceutical composition of EPO may be administered systemically to protect excitable tissue from damage, enhance the function of excitable tissue, or to deliver a compound to excitable tissue. Such administration may be parenterally, transmucosally, e.g., orally, nasally, rectally, intravaginally, sublingually, submucosally or transdermally. Preferably, administration is parenteral, e.g., via intravenous or intraperitoneal injection, and also including, but is not limited to, intra-arterial, intramuscular, intradermal and subcutaneous administration.

In a preferred embodiment, EPO may be administered systemically at a dosage between 2000-10000 Units/kg body weight, preferably about 2000-5000 Units/kg-body weight, most preferably 5000 Units/kg-body weight, per administration. This effective dose should be sufficient to achieve serum levels of EPO greater than about 10,000, 15,000, or 20,000 mU/ml of serum after EPO administration. Such serum levels may be achieved at about 1, 2, 3, 4, 5, 6, 7, 8, 9, or 10 hours post-administration. Such dosages may be repeated as necessary. For example, administration may be repeated daily, as long as clinically necessary, or after an appropriate interval, e.g., every 1 to 12 weeks, preferably, every 3 to 8 weeks. In one embodiment, the effective amount of EPO and a pharmaceutically acceptable carrier may be packaged in a single dose vial or other container. In one embodiment, an EPO is nonerythropoietic, i.e., it is capable of exerting the activities described herein but not causing an increase in hemoglobin concentration or hematocrit. In another embodiment, an EPO is given at a dose greater than that necessary to maximally stimulate erythropoiesis.

The pharmaceutical compositions of the invention may comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate-release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered via the nasal cavity to the lungs.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilised) condition requiring only the addition of a sterile liquid carrier, e.g., sterile saline solution for injections, immediately prior to use. Extemporaneous injection solutions and suspensions may be prepared from sterile powders, granules and tablets.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.4.2 Methods of Administration

The present invention provides compositions and methods for peripheral administration of EPO to enhance function or protect excitable tissues, and to deliver compounds to such tissues. As noted above, the present invention is based, in part, on the discovery that peripherally administered EPO has direct neuroprotective or neuroenhancement properties in excitable tissue, such as tissue of the central nervous system, peripheral nervous system, or heart tissue. Excitable tissue, as used herein, includes, but is not limited to, neuronal tissue of the central and peripheral nervous systems, and cardiac tissue. This section describes such compounds, and their methods for their of administration.

The present invention provides for administration of EPO and EPO receptor activity modulators by routes of administration other than directly into the central nervous system, and the terms "peripheral" and "systemic" subsumes these various routes. Peripheral administration includes oral or parenteral administration, such as intravenous, intraarterial, subcutaneous, intramuscular, intraperitoneal, rectal, submucosal or intradermal administration. Other routes are useful for the administration of the agents described herein. Both acute and chronic administration are provided herein.

In one embodiment, for example, EPO can be delivered in a controlled-release system. For example, the polypeptide may be administered using intravenous infusion, an implantable osmotic pump, a transdermal patch, liposomes, or other modes of administration. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, the compound can be delivered in a vesicle, in particular a liposome (see Langer, *Science* 249:

1527-1533 (1990); Treat et al., in Liposomes in the Therapy of Infectious Disease and Cancer, Lopez-Berestein and Fidler (eds.), Liss, New York, pp. 353-365 (1989); WO 91/04014; U.S. Pat. No. 4,704,355; Lopez-Berestein, ibid., pp. 317-327; see generally ibid.). In another embodiment, polymeric materials can be used [see Medical Applications of Controlled Release, Langer and Wise (eds.), CRC Press: Boca Raton, Fla., 1974; Controlled Drug Bioavailability, Drug Product Design and Performance, Smolen and Ball (eds.), Wiley: New York (1984); Ranger and Peppas, J. Macromol. Sci. Rev. Macromol. Chem. 23:61, 1953; see also Levy et al., 1985, Science 228:190; During et al., 1989, Ann. Neurol. 25:351; Howard et al., 1989, J. Neurosurg. 71:105).

In yet another embodiment, a controlled release system can be placed in proximity of the therapeutic target, i.e., the brain, thus requiring only a fraction of the systemic dose (see, e.g., Goodson, pp. 115-138 in Medical Applications of Controlled Release, vol. 2, supra, 1984). Other controlled release systems are discussed in the review by Langer (1990, Science 249:1527-1533).

In another embodiment, EPO, as properly formulated, can be administered by nasal, oral, rectal, vaginal, or sublingual administration.

In a specific embodiment, it may be desirable to administer the EPO compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

As is described hereinbelow, the studies that were performed by the inventors herein are standard, universally-accepted tests in animal models predictive of prophylactic and therapeutic benefit.

6. EXAMPLE 1

Peripherally Administered EPO Enhances Cognitive Function

In this Example, a spatial navigation experiment, known as the Morris Water Maze test, demonstrates EPO-induced enhancement of cognitive function in mice. In this test, a small transparent platform is placed in one quadrant of a swimming pool with opaque water. Mice placed into this swimming pool must swim until they reach the resting platform below the surface, which is invisible to the swimming mice. The test consists of measuring the time the animals take to get to the platform (i.e., the length of time they spend swimming). On successive trials, the time each mouse takes to reach the platform will decrease as a function of them learning its location. This type of learning experiment involves the hippocampus, as hippocampal lesions prevent learning in this test.

Experiments were carried out in a circular black pool, 150 cm in diameter. Four points were arbitrarily assigned: north, south, east and west. Distinctive visual cues were applied to each of these four quadrants: e.g., flashing lights, bright tape applied in squares etc., to orient the mice in the pool. A platform was arbitrarily placed in one quadrant. A trial consisted of placing the animal head-first in one quadrant of the pool and releasing it. The trial length was 90 seconds total. If the animal did not make it to the platform, she was placed on it for an additional 15 seconds. The subjects were rested for an hour, then placed in another quadrant for testing. All 4 quadrants were used over the course of a day's trials, and the animals were tested on 12 successive days (i.e., a total of 48 trials).

The experiment itself consisted of injecting each mice with 5000 U/kg recombinant human EPO (sold under the tradename of PROCRIT, Ortho-Biotech, Inc.) by intraperitoneal injection, 4 hours before the beginning of the day's testing, each day for the 12 trial days. Control animals were sham-injected with saline.

Learning was measured by measuring the length of time each mouse spent on the platform. Shown in FIG. 1A, the results are plotted as the time spent on the platform by the EPO-treated group and the sham group. As the results indicate, both groups of animals spent more time on the platform, i.e. they learned to reach the platform faster, on each successive trial day, but the EPO-treated animals did so faster than the sham group. Thus EPO-treated animals have a much faster "learning curve" than the sham group. When results were expressed as the difference between the EPO-treated and the sham-treated groups, and the results of the EPO and the sham-treated group were compared, the regression line ($R^2=0.88$) shows a slope (0.68) significantly different from a slope of 1, markedly in favor of the EPO group (FIG. 1B).

7. EXAMPLE 2

Peripherally Administered EPO Strengthens a Learned Conditioned Taste Aversion The Conditioned Taste Aversion (CTA) test performed in this Example demonstrates that EPO dramatically affects the ability of mice to remember, and learn to avoid, an unpleasant taste sensation, in this case an illness-provoking substance. In this example, lithium chloride is used to produce CTA, because lithium chloride reliably produces malaise and anorexia in a dose-dependent manner. Like a naturally occurring illness, lithium produces a CTA by stimulating the pathways described above, including cytokine release.

Female Balb/c mice were trained to limit their total daily water intake to a single 5 minute drinking period per day, and learned to drink enough water during this period to remain at equilibrium. Animals were divided into groups and administered either a sham control (saline) or EPO (5000 U/kg), injected intraperitoneally (IP), 4 hours before presentation of a novel saccharin-vanilla liquid. Immediately after finishing drinking the sweet liquid, animals received either saline or an illness-producing dose of lithium (20 mg/kg of a 0.15 M LiCl, delivered IP). Thereafter, three groups of animals were followed. The first group (control) did not receive lithium after drinking. The second group received both lithium and EPO. The third group (sham) received saline (without EPO) and lithium.

Conditioned Taste Aversion was measured by measuring the reduction in drinking upon subsequent exposure to the illness-producing solution, novel saccharin-vanilla liquid. After a 5-day recovery from the lithium or sham treatment, water-deprived animals were presented again with the same novel saccharin-vanilla liquid. The results plotted for groups 2 and 3, compared to 1 (control) are shown in FIG. 2A. Day 2 represents the baseline consumption of water after habituation to the test cage. On Day 3, animals received an intraperitoneal injection of either saline or EPO (5000 U/kg) 4 hrs before presentation of the novel saccharin-vanilla fluid, followed by treatment with lithium or a sham saline (arrow). This treatment resulted in a small decrease in fluid consumption in all groups on Day 3, a previously documented adverse effect of the injection and novelty of the fluid. After recovery, the first test for the establishment of a CTA showed no decrease in consumption for controls. However, animals having received lithium demonstrated a virtually complete aversion to the fluid, in spite of being water deprived (Day 4). Continued deprivation of water eventually produced an extinction of the CTA (Days 5 to 9), but was characterized by a markedly delayed recovery by the animals which had received EPO, as shown by the filled circles in FIG. 2A.

The robustness of the CTA established herein is better appreciated by considering the degree of water deficit present on each test day, as the EPO-treated animals tolerated a water deficit approximately twice that of sham-injected subjects (FIG. 2B). In spite of the markedly accentuated CTA demonstrated by the EPO group, the animals in this group more readily approached the drinking tube compared to the sham group, as shown in FIG. 2C. The strength of the CTA was demonstrated by a repeat injection of lithium alone (without EPO) which produced an attenuated CTA which was greater in the EPO group (FIG. 2A Day 10). These data show that EPO pre-treatment is associated with a markedly potentiated CTA produced by lithium.

8. EXAMPLE 3

Peripherally Administered EPO Protects Brain from an Excitotoxin

This Example demonstrates that EPO crosses the blood brain barrier and has a neuroprotective effect in mice treated with the neurotoxin kainate. Many compounds exist in nature which exhibit toxicity specifically for neurons. These molecules typically interact with endogenous receptors for the amino acid transmitter glutamate, subsequently causing excessive stimulation and neuronal injury. One of these, kainate, a substance widely used to study neuronal injury due to excitotoxicity, is an analogue of glutamate. Kainate is a potent neurotoxin which specifically destroys neurons, particularly those located in regions with a high density of kainate receptors, such as the hippocampus, and induces seizures, brain injury, and death.

The following neurotoxicity studies were performed with mice using kainate. This model is used to assess the protective benefit of treatments for conditions such as temporal lobe epilepsy. Parenteral injections in experimental animals such as rats and mice elicit partial (limbic) seizures in a dose-dependent manner, which then may generalize and cause death. The experiments presented in this section were performed to test whether peripherally-administered EPO crosses the blood brain barrier, and if so, whether EPO has an effect on neuronal energy balance, and specifically, it has neuroprotective effects against kainate.

To this end, female Balb/c mice (weighing on average 15-20 gm) were pretested with 5000 U/kg of recombinant human erythropoietin (rhEPO; sold under the mark PROCRIT, Ortho-Biotech, Inc.) or saline (sham) given intraperitoneally at specific time points before, at or after receiving kainate (Sigma Chemical), also IP, at specific concentrations (mass/kg-body weight). Subjects were then monitored and graded for the development of seizure activity at 20 minutes after receiving kainate. Each trial was terminated 60 minutes after the kainate dose. As shown in FIG. 3A, EPO pretreatment dramatically reduces seizure severity and delays the onset of status epilepticus in mice treated with kainate. The comparison between EPO- and sham-treated animals demonstrates a significantly lower death rate in animals receiving kainate dosages in the 20-30 mg/kg range, indicating neuroprotection afforded by pretreatment with EPO. The numbers in parentheses under each column indicate the number of animals exposed to each kainate dose.

The dose-dependency of EPO in providing neuroprotection from kainate is shown in FIG. 3B. Mice were administered EPO (5000 U/kg; IP daily for up to five days). The neuroprotective effect of each dose of EPO was assessed by determining survival after administration of kainate (20 mg/kg), which produces an approximate 50% mortality for control animals (no EPO; see FIG. 3A). Columns indicate improvement in survival of EPO-treated subjects, compared to sham-injected animals. As shown in FIG. 3B, neuroprotection increases with additional dosages of 5000 U/kg of EPO.

The neuroprotection provided by EPO is characterized by a delayed onset, characteristic of the activation of a gene expression program. FIG. 3C shows the EPO-related delay (in minutes) in death from seizures of a single dose of EPO given at the time of kainate administration (20 mg/kg) does not provide any immediate protection, whereas EPO given 24 hours before kainate improves the latency and severity of seizures and time to death. This effect lasts for up to 7 days.

9. EXAMPLE 4

Peripherally Administered EPO Protects Brain from Damage Due to Ischemia

Previous in vivo studies using a global reperfusion model in the gerbil, have indicated that stopping blood flow to the brain results in cell death in the brain, and that EPO injected directly into the cerebral ventricles protects the brain from such cell death (Sakanaka et al., 1998, Proc. Natl. Acad. Sci. U.S.A. 95:4635). The experiments presented in this Example, for the first time, show that EPO delivered peripherally protects the neural cell death in vivo in an animal model of ischemia.

The following experiment was performed using the middle cerebral artery occlusion model, an art-accepted model of ischemic focal stroke. In the protocol, male rats (250 gm of body weight) were anesthetized with phenobarbital, and maintained at 37° C. The carotid arteries were visualized, and the ipsalateral carotid artery permanently occluded. The ipsalateral middle cerebral artery (MCA) was visualized and cauterized at its origin. The contralateral artery was occluded by clamping for 1 hour. Animals were sacrificed 24 hours later, and the brain removed and sectioned into 1 mm serial sections. Viable tissue was visualized by in situ triphenyltetrazolium reduction to visualize live tissue from necrotic regions. The ischemic core, and the surrounding penumbra, undergoes cell death.

Using this MCA model, EPO was administered by parenteral injections at various times before and immediately after the injury, and the volume of the injury was quantified by computer-assisted image analysis. The results of this analysis, shown in FIG. 4A, indicated the effect of treatment with EPO at the following times after the stroke: 24 hours before the stroke, at the time of the stroke, and 3, 6, and 9 hours after the stroke. As shown in FIG. 4A, EPO protects tissue from necrotic injury when administered up to 6 hours post stroke.

Interestingly and in contrast, a 17-mer derived from EPO, which had been previously reported to have neurotropic activity, promoting neurite growth in vitro and nerve cell myelination ex vivo (Campana et al., 1998, Int. J. Mol. Med. 1:235-41; U.S. Pat. No. 5,700,909 issued Dec. 23, 1997), had no effect in protection against injury in this system (FIG. 4B, "17-mer"). Thus, this model, as well as the other methods for assaying the effect of EPO on excitable tissue function provided by the present invention, can be used to identify EPO and EPO receptor activity modulators which can be used to modulate excitable tissue function, such as protection from injury, or enhancement of learning and cognition.

10. EXAMPLE 5

Peripherally Administered EPO Protects Brain from Blunt Trauma

In a model of mechanical trauma, the cortical impact model, pretreatment with systemically-administered EPO protects mouse brain from blunt trauma. To induce trauma a pneumatically-driven piston (Clippard Valves), 3 mm in diameter which can precisely deliver a blow to the skull was employed. Each mouse was anesthetized and placed securely in a sterotaxic device, to prevent the head from moving. A scalp incision was made in order to determine the location of the bregma, which is the reference point with which the piston was initially positioned. The piston was then adjusted by moving it 2 mm caudal and 2 mm ventral to bregma and the impact made by use of a precise pulse of nitrogen. This device allows for a precise selection of piston velocity (4 m/s) and impact displacement (2 mm).

Mice were treated with EPO (5000 U/kg) 24 hours before, at the time of injury, 3, 6, or 9 hours later and continued as daily dosages. Mice were sacrificed 10 days after the procedure, and the brains subsequently examined and the volume of brain necrosis determined. In sham-treated mice, a large area of necrosis was observed (FIG. 5), and with abundant infiltration of monocytes. In contrast, animals are protected from such damage, and few mononuclear cells were detected in the area of injury, when animals are pre-treated with EPO or given EPO up to 3 hours after injury.

11. EXAMPLE 6

Peripherally Administered EPO Protects Myocardium from Ischemic Injury

This Example demonstrates the effect of EPO in protection of heart tissue against hypoxic injury. To accomplish this, rats were pretested with EPO (5000 U/kg) 24 hours before the procedure performed as per Latini et al., (1999, J. Cardiovasc. Pharmacol. 31:601-8). Subsequently, subjects were anesthetized, placed on assisted ventilation and a thoracotomy performed. The heart and its intrinsic circulation is identified and a removable suture placed around the most proximal portion of the left anterior descending coronary artery and then ligated. An additional dose of EPO (5000 U/kg) was then given and the occlusion maintained for 30 minutes. At this time, the ligature was loosened and the animal is maintained under deep anesthesia for an additional 6 hours and subsequently sacrificed. Immediately after death, the heart was removed and a portion of the affected region (AAR) as well as unaffected region (septum) was removed and prepared for biochemical analyses. Two parameters were assessed, creatine kinase (CK) as a measure of the survival of myocardium (the lower the CK, the less viable the tissue) and myeloperoxidase, which is a product of mononuclear cell infiltrate. The results are shown in FIG. 6A and FIG. 6B. As indicated in these figures, treatment with EPO results in maintained CK activity, consistent with an increase in tissue viability, and decreased MPO activity, relative to the control, in both the infarct area (AAR) and the perfused left ventricle (LV) free wall, indicating that there is significantly less infiltration by inflammatory cells.

12. EXAMPLE 7

Peripherally Administered EPO Attenuates Experimental Allergic Encephalitis

Experimental allergic (or autoimmune) encephalomyelitis (EAE) in rats, is an art accepted animal model for multiple sclerosis (MS). Various animal models with EAE have been developed applying immunologic, virologic, toxic and traumatic parameters in order to understand features of MS.

To test whether EPO protects against symptoms of EAE, the following experiment was performed. Female Lewis rats, 6-8 weeks of age (Charles River, Calco, Italy) were immunized under light ether anesthesia by injecting into both hind footpads 50 µg of guinea pig myelin basic protein (MBP; Sigma, St. Louis, Mo.) in water, emulsified in equal volumes of complete Freund's adjuvant (CFA, Sigma) with 7 mg/ml of heat-killed *Mycobacterium tuberculosis* added to H37Ra (Difco, Detroit, Mich.) in a final volume of 100 µl.

After treatments, rats were assessed daily for signs of experimental autoimmune encephalomyelitis (EAE) and scored as follows: 0, no disease; 1, flaccid tail; 2, ataxia; 3, complete hind limb paralysis with urinary incontinence. Body weights were also monitored. Rats were administered EPO (5000 U/kg, IP, once daily) starting on day 3 post-immunization and continued until day 18. Control rats received vehicles alone. As shown in FIG. 7, rats treated with EPO demonstrated an improvement in score (i.e., a lower number) and in the duration of the disease. In addition, a marked delay in the onset of symptoms was noticed in rats treated with EPO.

13. EXAMPLE 8

Minimum Effective Dose and Pharmacokinetics of EPO Required for Protection of Excitable Tissue Optimum and effective dosages of EPO was assessed using the animal model of focal ischemia stroke described above. As shown in FIG. 8A, an EPO dosage of less than 450 Units/kg body weight was not reliably effective in protecting excitable tissue from necrotic injury. As shown in FIG. 8B, in animal studies, a dose of approximately 5000 Units/kg-body weight delivered IP to four female mouse subjects resulted in a circulating level of EPO greater than 20,000 mUnits/ml of serum within 5 hours after its administration, greater than 10,000 mUnits after 10 hours post administration, but less than 5 Units/ml 24 hours after administration.

14. EXAMPLE 9

CNS Delivery Mediated by Erythropoietin

The experiments presented hereinbelow indicate the successful transport of a molecule conjugated to EPO across the blood-brain barrier and its localization inside basement membrane. As shown in FIG. 9A, brain sections were stained with antibodies for EPO receptor (EPO-R), which shows that brain capillaries express high levels of EPO-R. In order to study whether EPO is can be transported across the blood-brain barrier, EPO was labeled with biotin as follows. The volume containing rhEPO was concentrated using a Centricon-10 filter (Millipore), and recovery measured by reading the absorbance reading at a wavelength of 280 nm. Next, 0.2 mg of long arm biotin (Vector Labs) was dissolved in 100 µl of DMSO, added to the concentrated rhEPO solution and vortexed immediately. This mixture was then incubated at room temperature for four hours, while gently stirring and protected from light. Unbound biotin was removed from the solution by using a Centricon-10 column. Biotinylated EPO was then administered to animals IP, and 5 hours later the animals were sacrificed. Brain sections were labeled with avidin coupled to peroxidase, and diaminobenzidine added until sufficient reaction product developed for observation by light microscopy. EPO was found along the same capillaries that stained positive for EPO-R (FIG. 9B). At later time points, the biotin label appeared localized within specific neurons (e.g., 17 hours, FIG. 9C). In contrast, if cold EPO was added in 1000 time excess to labeled EPO, all specific staining was eliminated. The results demonstrate the successful delivery of a systemically administered conjugated EPO compound across the blood brain barrier.

Successful delivery of a systemically administered EPO-biotin conjugate across the blood brain barrier into the brain demonstrates that other therapeutic compounds can be delivered across the blood-brain barrier in similar fashion, by complexing EPO to the compound of interest. As one example, brain-derived neurotrophic factor (BNF) can be covalently coupled to EPO by carbodiimide coupling using standard procedures. After purification, the conjugate can administered to animals via intraperitoneal injection. Positive effects of BNF on the central nervous system can be measured relative to control animals, to measure the successful transport of this molecule in association with EPO, in contrast to the lack of a central nervous system activity by unconjugated BNF.

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein are incorporated by reference herein in their entireties for all purposes.

What is claimed is:

1. A method for treating or protecting against injury or damage to heart tissue due to myocardial infarction, cardiac arrest, cardiac ischemia, cardiac inflammation, dysrhythmia, or cardiac trauma in mammals, comprising administering peripherally to a mammal in need thereof a non-toxic amount of EPO effective for the protection or treatment of the heart tissue.

2. The method of claim 1 wherein said injury or damage is the result of a myocardial infarction.

3. The method of claim 1 wherein said administration comprises oral, topical, intraluminal or by inhalation or parenteral administration.

4. The method of claim 3 wherein said parenteral administration is intravenous, intraarterial, subcutaneous, intramuscular, intraperitoneal, submucosal or intradermal.

5. The method of claim 1 wherein said administration is acute or chronic.

6. The method of claim 1 wherein said EPO is administered at a dose greater than the dose necessary to maximally stimulate erythropoiesis.

7. The method of claim 1 wherein said EPO is a recombinant form of erythropoietin.

8. The method of claim 1 wherein the injury or damage is the result of a cardiac arrest, cardiac ischemia, cardiac inflammation, dysrhythmia, or cardiac trauma.

* * * * *